(12) United States Patent
Edwin et al.

(10) Patent No.: US 8,313,524 B2
(45) Date of Patent: *Nov. 20, 2012

(54) SELF-SEALING PTFE GRAFT WITH KINK RESISTANCE

(75) Inventors: Tarun J. Edwin, Chandler, AZ (US); Jamie Abbott, Mesa, AZ (US); Heidi R. Cole, Chandler, AZ (US); Chandrashekhar P. Pathak, Phoenix, AZ (US); David L. Bogert, Phoenix, AZ (US); Richard Elton, Glens Falls, NY (US); Fitzroy Brown, Chandler, AZ (US); Kereshmeh Shahriari, Phoenix, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 710 days.

This patent is subject to a terminal disclaimer.

(21) Appl. No.: 11/661,250

(22) PCT Filed: Aug. 30, 2005

(86) PCT No.: PCT/US2005/031186
§ 371 (c)(1),
(2), (4) Date: Mar. 27, 2007

(87) PCT Pub. No.: WO2006/026725
PCT Pub. Date: Mar. 9, 2006

(65) Prior Publication Data
US 2008/0027534 A1    Jan. 31, 2008

Related U.S. Application Data

(60) Provisional application No. 60/605,770, filed on Aug. 31, 2004, provisional application No. 60/692,172, filed on Jun. 17, 2005.

(51) Int. Cl.
*A61F 2/06* (2006.01)

(52) U.S. Cl. ............... 623/1.44; 623/1.31; 623/1.32
(58) Field of Classification Search ............ 285/334.5, 285/234; 623/1.32–1.33, 1.44, 1.1, 1.13, 623/1.22, 1.28, 1.31, 1.34, 1.39, 1.4, 1.42, 623/1.46; 604/8
See application file for complete search history.

(56) References Cited

U.S. PATENT DOCUMENTS 3,105,492 A * 10/1963 Jeckel .................... 623/1.44
(Continued)

FOREIGN PATENT DOCUMENTS
EP    0203833 A1    12/1986
(Continued)

OTHER PUBLICATIONS

James et al., "In Vivo Patency of Endothelial Cell-Lined ePTFE Prostheses in an Ovine Model"; Artif Organs, Aug. 1992; 16(4):346-53.

(Continued)

*Primary Examiner* — David Isabella
*Assistant Examiner* — Andrew Iwamaye
(74) *Attorney, Agent, or Firm* — Rutan & Tucker, LLP

(57) ABSTRACT

A self-sealing vascular graft, including a substrate with a sealant layer and several optional additional layers, is described. The substrate can be ePTFE and the material used for the sealant and additional layers can be polyurethane. The sealant layer and additional layers may include one or more base layers, one or more foam layers, beading of different sizes and shapes, and ePTFE tape. A flared cuff may be integral to one or both ends of the substrate or may be attached to one or both ends. Various methods of making a self-sealing vascular graft are also described, including methods of disposition, methods of forming, methods of bonding and methods of attaching.

11 Claims, 13 Drawing Sheets

U.S. PATENT DOCUMENTS

| | | | |
|---|---|---|---|
| 4,130,904 A * | 12/1978 | Whalen | 623/1.44 |
| RE31,618 E | 7/1984 | Mano et al. | |
| 4,550,447 A * | 11/1985 | Seiler et al. | 623/1.32 |
| 4,604,762 A | 8/1986 | Robinson | |
| 4,619,641 A * | 10/1986 | Schanzer | 604/8 |
| 4,718,907 A | 1/1988 | Karwoski et al. | |
| 4,731,073 A | 3/1988 | Robinson | |
| 4,733,665 A | 3/1988 | Palmaz | |
| 4,739,013 A | 4/1988 | Pinchuk | |
| 4,743,252 A | 5/1988 | Martin, Jr. et al. | |
| 4,810,749 A | 3/1989 | Pinchuk | |
| 4,816,339 A | 3/1989 | Tu et al. | |
| 4,857,069 A | 8/1989 | Kira et al. | |
| 4,955,296 A | 9/1990 | Barlow | |
| 4,955,899 A | 9/1990 | Della Corna et al. | |
| 4,990,138 A | 2/1991 | Bacich et al. | |
| 5,024,671 A | 6/1991 | Tu et al. | |
| 5,061,276 A | 10/1991 | Tu et al. | |
| 5,116,360 A | 5/1992 | Pinchuk et al. | |
| 5,133,742 A | 7/1992 | Pinchuk | |
| 5,148,806 A | 9/1992 | Fukui et al. | |
| 5,152,782 A | 10/1992 | Kowligi et al. | |
| 5,192,310 A | 3/1993 | Herweck et al. | |
| 5,201,314 A | 4/1993 | Bosley, Jr. et al. | |
| 5,229,431 A | 7/1993 | Pinchuk | |
| 5,269,810 A | 12/1993 | Hull et al. | |
| 5,319,059 A | 6/1994 | Neuenschwander et al. | |
| 5,354,329 A | 10/1994 | Whalen | |
| 5,453,235 A | 9/1995 | Calcote et al. | |
| 5,462,781 A | 10/1995 | Zukowski | |
| 5,464,438 A | 11/1995 | Menaker | |
| 5,507,769 A * | 4/1996 | Marin et al. | 606/198 |
| 5,527,353 A | 6/1996 | Schmitt | |
| 5,556,426 A | 9/1996 | Popadiuk et al. | |
| 5,607,442 A | 3/1997 | Fischell et al. | |
| 5,607,478 A | 3/1997 | Lentz et al. | |
| 5,609,624 A | 3/1997 | Kalis | |
| 5,620,763 A | 4/1997 | House et al. | |
| 5,628,782 A | 5/1997 | Myers et al. | |
| 5,628,786 A | 5/1997 | Banas et al. | |
| 5,641,373 A | 6/1997 | Shannon et al. | |
| 5,641,443 A | 6/1997 | Calcote et al. | |
| 5,665,114 A | 9/1997 | Weadock et al. | |
| 5,700,287 A * | 12/1997 | Myers et al. | 623/1.38 |
| 5,707,386 A | 1/1998 | Schnepp-Pesch et al. | |
| 5,716,393 A | 2/1998 | Lindenberg et al. | |
| 5,716,395 A | 2/1998 | Myers et al. | |
| 5,716,660 A | 2/1998 | Weadock et al. | |
| 5,800,510 A | 9/1998 | Schmitt | |
| 5,800,512 A | 9/1998 | Lentz et al. | |
| 5,817,017 A | 10/1998 | Young et al. | |
| 5,824,050 A | 10/1998 | Karwoski et al. | |
| 5,827,327 A | 10/1998 | McHaney et al. | |
| 5,840,240 A | 11/1998 | Stenoien et al. | |
| 5,843,171 A | 12/1998 | Campbell et al. | |
| 5,843,173 A | 12/1998 | Shannon et al. | |
| 5,851,229 A | 12/1998 | Lentz et al. | |
| 5,851,230 A | 12/1998 | Weadock et al. | |
| 5,860,999 A | 1/1999 | Schnepp-Pesch et al. | |
| 5,861,026 A | 1/1999 | Harris et al. | |
| 5,866,217 A | 2/1999 | Stenoien et al. | |
| 5,897,587 A | 4/1999 | Martakos et al. | |
| 5,904,967 A * | 5/1999 | Ezaki et al. | 428/36.92 |
| 5,910,168 A | 6/1999 | Myers et al. | |
| 5,931,865 A * | 8/1999 | Silverman et al. | 138/103 |
| 5,976,192 A | 11/1999 | McIntyre et al. | |
| 6,001,125 A | 12/1999 | Golds et al. | |
| 6,010,529 A | 1/2000 | Herweck et al. | |
| 6,019,787 A | 2/2000 | Richard et al. | |
| 6,019,788 A * | 2/2000 | Butters et al. | 623/1.35 |
| 6,022,335 A | 2/2000 | Ramadan | |
| 6,036,724 A | 3/2000 | Lenz et al. | |
| 6,039,755 A | 3/2000 | Edwin et al. | |
| 6,042,666 A | 3/2000 | Karwoski et al. | |
| 6,048,362 A | 4/2000 | Berg | |
| 6,053,941 A | 4/2000 | Lindenberg et al. | |
| 6,053,943 A * | 4/2000 | Edwin et al. | 623/1.25 |
| 6,056,970 A | 5/2000 | Greenawalt et al. | |
| 6,080,198 A | 6/2000 | Lentz et al. | |
| 6,099,557 A | 8/2000 | Schmitt | |
| 6,102,884 A * | 8/2000 | Squitieri | 604/8 |
| 6,120,532 A | 9/2000 | Goldfarb | |
| 6,124,523 A | 9/2000 | Banas et al. | |
| 6,162,244 A * | 12/2000 | Braun et al. | 623/1.12 |
| 6,174,330 B1 | 1/2001 | Stinson | |
| 6,187,038 B1 * | 2/2001 | Sullivan et al. | 623/1.43 |
| 6,187,039 B1 * | 2/2001 | Hiles et al. | 623/1.44 |
| 6,190,590 B1 | 2/2001 | Randall et al. | |
| 6,200,338 B1 | 3/2001 | Solomon et al. | |
| 6,203,568 B1 | 3/2001 | Lombardi et al. | |
| 6,203,735 B1 | 3/2001 | Edwin et al. | |
| 6,221,101 B1 | 4/2001 | Harris et al. | |
| 6,253,769 B1 | 7/2001 | LaFontaine et al. | |
| 6,261,257 B1 | 7/2001 | Uflacker et al. | |
| 6,267,834 B1 | 7/2001 | Shannon et al. | |
| 6,270,523 B1 | 8/2001 | Herweck et al. | |
| 6,273,912 B1 * | 8/2001 | Scholz et al. | 623/1.31 |
| 6,285,739 B1 | 9/2001 | Rudin et al. | |
| 6,287,337 B1 | 9/2001 | Martakos et al. | |
| 6,315,791 B1 | 11/2001 | Gingras et al. | |
| 6,319,279 B1 | 11/2001 | Shannon et al. | |
| 6,328,762 B1 * | 12/2001 | Anderson et al. | 623/1.41 |
| 6,355,063 B1 | 3/2002 | Calcote | |
| 6,368,347 B1 | 4/2002 | Maini et al. | |
| 6,379,381 B1 | 4/2002 | Hossainy et al. | |
| 6,383,214 B1 | 5/2002 | Banas et al. | |
| 6,416,537 B1 | 7/2002 | Martakos et al. | |
| 6,428,571 B1 * | 8/2002 | Lentz et al. | 623/1.4 |
| 6,436,135 B1 | 8/2002 | Goldfarb | |
| 6,451,047 B2 | 9/2002 | McCrea et al. | |
| 6,514,196 B1 | 2/2003 | Sullivan et al. | |
| 6,534,084 B1 | 3/2003 | Vyakarnam et al. | |
| 6,547,820 B1 | 4/2003 | Staudenmeier | |
| 6,572,647 B1 | 6/2003 | Supper et al. | |
| 6,589,278 B1 | 7/2003 | Harris et al. | |
| 6,589,468 B1 | 7/2003 | Schmitt | |
| 6,596,023 B1 * | 7/2003 | Nunez et al. | 623/1.3 |
| 6,660,301 B1 | 12/2003 | Vogel et al. | |
| 6,673,102 B1 | 1/2004 | Vonesh et al. | |
| 6,676,700 B1 | 1/2004 | Jacobs et al. | |
| 6,712,919 B2 | 3/2004 | Ruefer et al. | |
| 6,716,239 B2 | 4/2004 | Sowinski et al. | |
| 6,719,783 B2 | 4/2004 | Lentz et al. | |
| 6,726,696 B1 | 4/2004 | Houser et al. | |
| 6,746,480 B2 | 6/2004 | Scholz et al. | |
| 6,756,007 B2 | 6/2004 | Pletzer et al. | |
| 6,786,920 B2 * | 9/2004 | Shannon et al. | 623/1.13 |
| 6,790,226 B2 | 9/2004 | Edwin et al. | |
| 6,797,217 B2 | 9/2004 | McCrea et al. | |
| 6,814,753 B2 | 11/2004 | Schmitt | |
| 6,821,295 B1 | 11/2004 | Farrar | |
| 6,827,737 B2 | 12/2004 | Hill et al. | |
| 6,863,686 B2 | 3/2005 | Shannon et al. | |
| 6,926,735 B2 | 8/2005 | Henderson | |
| 7,244,271 B2 | 7/2007 | Lentz et al. | |
| 7,468,071 B2 | 12/2008 | Edwin et al. | |
| 8,066,758 B2 | 11/2011 | Bogert et al. | |
| 2001/0018609 A1 * | 8/2001 | Smith | 623/1.13 |
| 2001/0021870 A1 | 9/2001 | Edwin et al. | |
| 2002/0065552 A1 * | 5/2002 | Jayaraman et al. | 623/1.46 |
| 2002/0091439 A1 | 7/2002 | Baker et al. | |
| 2002/0095205 A1 | 7/2002 | Edwin et al. | |
| 2002/0138136 A1 | 9/2002 | Chandresekaran et al. | |
| 2002/0193869 A1 | 12/2002 | Dang | |
| 2002/0198559 A1 | 12/2002 | Mistry et al. | |
| 2003/0004559 A1 | 1/2003 | Lentz et al. | |
| 2003/0004563 A1 | 1/2003 | Jackson et al. | |
| 2003/0017775 A1 | 1/2003 | Sowinski et al. | |
| 2003/0027775 A1 | 2/2003 | Wallace | |
| 2003/0100859 A1 * | 5/2003 | Henderson et al. | 604/8 |
| 2003/0139799 A1 | 7/2003 | Ley et al. | |
| 2003/0139806 A1 | 7/2003 | Haverkost et al. | |
| 2003/0149471 A1 * | 8/2003 | Briana et al. | 623/1.13 |
| 2003/0204242 A1 * | 10/2003 | Zarins et al. | 623/1.16 |
| 2004/0015228 A1 | 1/2004 | Lombardi et al. | |
| 2004/0024442 A1 | 2/2004 | Sowinski et al. | |
| 2004/0033364 A1 | 2/2004 | Spiridigliozzi et al. | |

| | | | |
|---|---|---|---|
| 2004/0049264 A1 | 3/2004 | Sowinski et al. | |
| 2004/0054406 A1 | 3/2004 | Dubson et al. | |
| 2004/0064181 A1 | 4/2004 | Harris et al. | |
| 2004/0082989 A1* | 4/2004 | Cook et al. | 623/1.13 |
| 2004/0122507 A1 | 6/2004 | Henderson | |
| 2004/0122509 A1 | 6/2004 | Brodeur | |
| 2004/0164445 A1 | 8/2004 | Nieman et al. | |
| 2004/0182511 A1 | 9/2004 | Rakos et al. | |
| 2004/0193242 A1 | 9/2004 | Lentz et al. | |
| 2004/0210302 A1 | 10/2004 | Scholz et al. | |
| 2004/0215337 A1 | 10/2004 | Hain et al. | |
| 2004/0232588 A1 | 11/2004 | Edwin et al. | |
| 2004/0236400 A1 | 11/2004 | Edwin et al. | |
| 2004/0244442 A1 | 12/2004 | Shiao et al. | |
| 2005/0004653 A1 | 1/2005 | Gerberding et al. | |
| 2005/0015138 A1 | 1/2005 | Schuessler et al. | |
| 2005/0064224 A1 | 3/2005 | Bavaro et al. | |
| 2005/0096721 A1 | 5/2005 | Mangin et al. | |
| 2005/0246012 A1 | 11/2005 | Henderson | |
| 2006/0116755 A1* | 6/2006 | Stinson | 623/1.44 |
| 2006/0259133 A1 | 11/2006 | Sowinski et al. | |
| 2007/0123968 A1 | 5/2007 | Weinberg | |
| 2007/0204445 A1* | 9/2007 | Hood et al. | 28/143 |
| 2007/0244539 A1 | 10/2007 | Lentz et al. | |
| 2009/0171436 A1 | 7/2009 | Casanova et al. | |
| 2010/0179642 A1 | 7/2010 | Bogert et al. | |
| 2011/0125253 A1 | 5/2011 | Casanova et al. | |
| 2012/0061001 A1 | 3/2012 | Bogert et al. | |

FOREIGN PATENT DOCUMENTS

| | | |
|---|---|---|
| EP | 1371345 A2 | 12/2003 |
| JP | 2000501961 A | 2/2000 |
| JP | 2000167063 A | 6/2000 |
| JP | 2000171595 A | 6/2000 |
| JP | 2000217903 A | 8/2000 |
| JP | 2002501779 T | 1/2002 |
| JP | 2002540854 T | 12/2002 |
| JP | 2003511196 A | 3/2003 |
| JP | 2003284781 A | 10/2003 |
| JP | 2006511283 A | 4/2006 |
| JP | 2006514557 A | 5/2006 |
| JP | 2006527630 A | 12/2006 |
| WO | 9003036 A1 | 3/1990 |
| WO | 9703812 A1 | 2/1997 |
| WO | 9721401 A1 | 6/1997 |
| WO | 9826731 A2 | 6/1998 |
| WO | 0128456 A1 | 4/2001 |
| WO | 0149340 A1 | 7/2001 |
| WO | 0158504 | 8/2001 |
| WO | 2004011055 A2 | 2/2004 |
| WO | 2004021931 A1 | 3/2004 |
| WO | 2004096307 A1 | 11/2004 |

OTHER PUBLICATIONS

Kohler et al., "Dialysis Access Failure: A Sheep Model of Rapid Stenosis", J Vasc Surg., Oct. 1999; 30(4):744-51.

Tillman et al, "Platelet Function and Coagulation Parameters in Sheep During Experimental Vascular Surgery", Lab Anim Sci., Jun. 1981; 31(3):263-7.

EP 06839788.4 filed on Aug. 5, 2008 EP Search Report dated Dec. 28, 2009.

EP 06839788.4 filed on Aug. 5, 2008 Office Action dated Jul. 13, 2010.

PCT/US2006/060704 filed on Nov. 9, 2006 International Preliminary Report on Patentability dated May 14, 2006.

PCT/US2006/060704 filed on Nov. 9, 2006 Search Report dated Nov. 1, 2007.

PCT/US2006/060704 filed on Nov. 9, 2006 Written Opinion dated Nov. 1, 2007.

JP 2007-530364 filed Aug. 30, 2005 Office Action dated Oct. 19, 2010.

PCT/US2005/031186 filed Aug. 30, 2005 International Preliminary Report on Patentability dated Feb. 28, 2007.

PCT/US2005/031186 filed Aug. 30, 2005 Search Report dated Feb. 6, 2007.

PCT/US2005/031186 filed Aug. 30, 2005 Written Opinion dated Feb. 6, 2007.

PCT/US2005/046763 filed Dec. 28, 2005 International Preliminary Report on Patentability dated Dec. 17, 2007.

PCT/US2005/046763 filed Dec. 28, 2005 Search Report dated Apr. 30, 2007.

PCT/US2005/046763 filed Dec. 28, 2005 Written Opinion dated Apr. 30, 2007.

U.S. Appl. No. 11/917,135, filed Jan. 17, 2008 Non-Final Office Action dated Nov. 26, 2010.

EP 06839787.6 filed on Nov. 11, 2006 EP Search Report dated Jan. 12, 2010.

JP 2008-516811 filed Dec. 28, 2005 Office Action dated Mar. 28, 2011.

JP 2008-540337 filed Apr. 27, 2006 Office Action dated Apr. 6, 2012.

JP 2008-540337 filed Apr. 27, 2006 Office Action dated Nov. 24, 2011.

JP 2008-540338 filed Apr. 27, 2006 Office Action dated Sep. 30, 2011.

PCT/US2006/060702 filed on Nov. 11, 2006 International Preliminary Report on Patentability dated May 14, 2008.

PCT/US2006/060702 filed on Nov. 11, 2006 Search Report dated Dec. 28, 2007.

PCT/US2006/060702 filed on Nov. 11, 2006 Written Opinion dated Dec. 28, 2007.

U.S. Appl. No. 11/917,135, filed Jan. 17, 2008 Final Office Action dated May 9, 2011.

U.S. Appl. No. 12/092,561, filed Sep. 17, 2008 Final Office Action dated Jun. 15, 2012.

U.S. Appl. No. 12/092,561, filed Sep. 17, 2008 Non-Final Office Action dated Jan. 4, 2012.

EP 05855344.7 filed Dec. 28, 2005 Extended European Search Report dated Aug. 14, 2012.

* cited by examiner

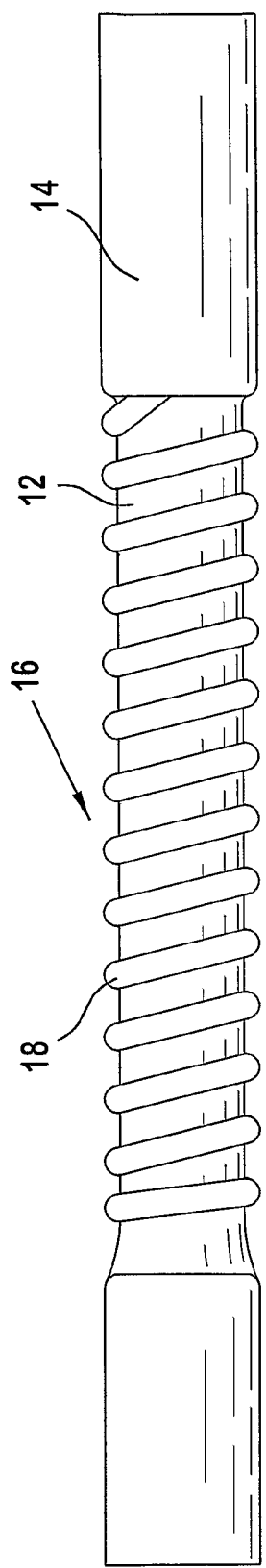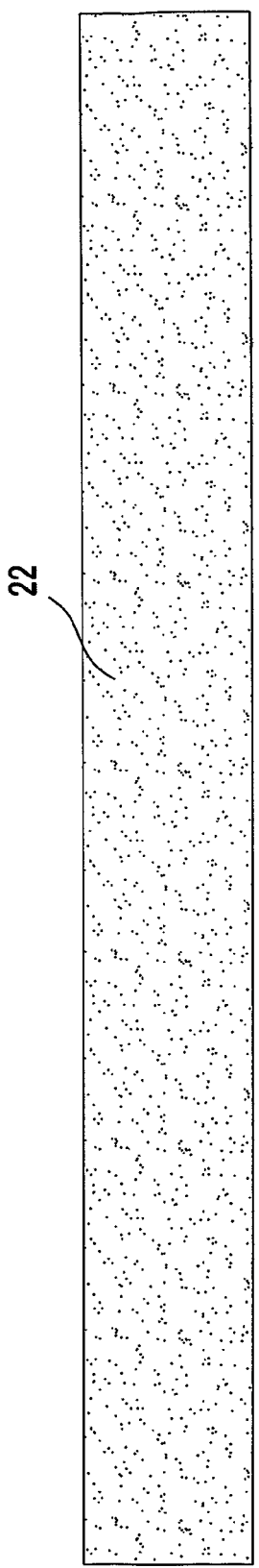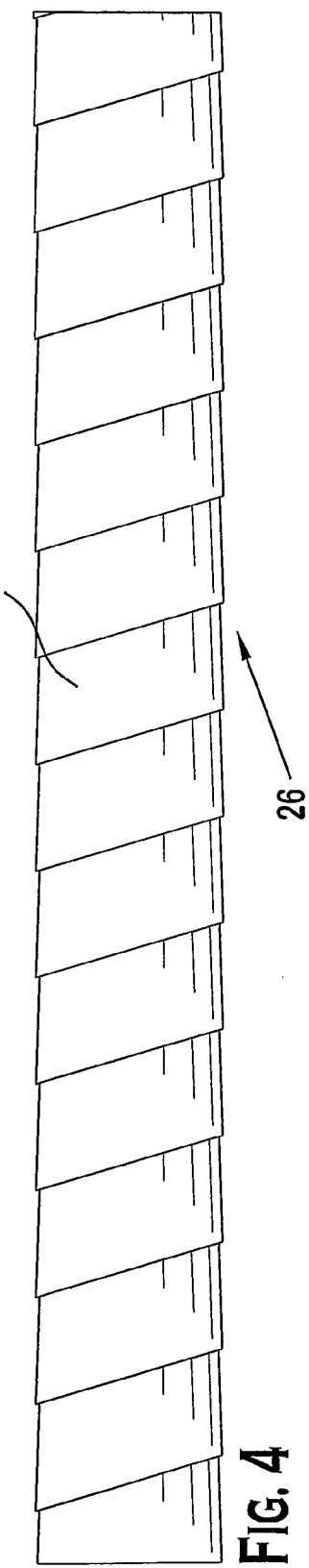
FIG. 2
FIG. 3
FIG. 4

SELF-SEALING PTFE GRAFT WITH KINK RESISTANCE

PRIORITY

This application is a United States national stage application under 35 USC §371 of International Patent Application No. PCT/US05/31186, filed Aug. 30, 2005, which claims the benefit of priority to U.S. Provisional Application No. 60/605,770, filed Aug. 31, 2004, and U.S. Provisional Application No. 60/692,172, filed Jun. 17, 2005, each of which is incorporated by reference into this application as if fully set forth herein.

BACKGROUND OF THE INVENTION

Patients suffering from reduced renal function or renal failure often have to undergo hemodialysis treatments. During dialysis, blood is withdrawn from the patient and is circulated through a hemodialysis machine. The machine removes toxic waste products and returns the purified blood to the patient. Typically, dialysis treatments are performed three times a week for the duration of a patient's life unless a kidney transplant procedure occurs. To successfully undergo hemodialysis treatment, blood must be circulated through the hemodialysis machine at 150 to 600 ml/minute or higher flow rate for about 3-4 hours. Blood flow from the venous system is believed to be inadequate to meet the required flow rate and repeated punctures of large arteries are not feasible. Therefore, native fistulas are often created to provide blood flow access for the hemodialysis machines.

If native fistulas are unavailable or cannot be used for hemodialysis, then vascular grafts, typically made from expanded polytetrafluoroethylene (ePTFE) tubes, are surgically placed between an artery and a vein (ePTFE AV grafts). This procedure is especially useful in patients who do not have blood vessels that will support the construction of a more traditional primary native fistula in the forearm. The ePTFE AV grafts, which are extruded, are favored over textile AV grafts, which are woven, knitted, braided or otherwise formed, for several reasons, including the unique microstructure characterized by nodes and fibrils imparted to the ePTFE grafts, which facilitates tissue ingrowth while simultaneously providing a fluid-tight conduit through which blood can flow; and the ability to provide a graft with a relatively thin wall while retaining necessary strength characteristics.

Expanded polytetrafluoroethylene AV grafts are extensively used for hemodialysis treatments as AV bridge fistulae due, at least in part, to the hemocompatibility advantage of the ePTFE material over other materials (such as polyurethane). However, one potential drawback in using ePTFE AV grafts is that they cannot be used safely to withdraw blood for hemodialysis until about 14 days post-implant. This is believed to be due to the non-elastomeric nature of ePTFE, which cannot self-seal upon puncturing. Thus, in the interim, other means of dialysis must be employed (e.g., hemodialysis catheters, etc.). After 14 days, there is typically sufficient tissue ingrowth into the ePTFE surface to act as a sealant layer, and therefore the graft can seal the puncture wound created by removal of the dialysis needle. However, such sealing requires a combination of pressure and hemostasis, which does not lend to uniformity due to the many variables present during such procedures (dialysis technician/nurse skill level, operating conditions, etc.). It is therefore preferable to have a sealing mechanism for an ePTFE vascular graft that is not dependent on hemostasis and the attendant variables associated therewith and which will seal immediately upon implantation so that additional methods of dialysis do not have to be employed.

Accordingly, various sealing techniques, such as placing a layer of elastomeric sealant on ePTFE, and composite structures have been shown or described to provide immediate self-sealing properties to an ePTFE AV graft. Examples of various types of elastomeric sealants, ePTFE grafts, self-sealing grafts, and composite grafts include those disclosed in the following U.S. patents and published applications: U.S. Pat. No. Re. 31,618, U.S. Pat. No. 4,604,762; U.S. Pat. No. 4,619,641; U.S. Pat. No. 4,731,073; U.S. Pat. No. 4,739,013; U.S. Pat. No. 4,743,252; U.S. Pat. No. 4,810,749; U.S. Pat. No. 4,816,339; U.S. Pat. No. 4,857,069; U.S. Pat. No. 4,955,899; U.S. Pat. No. 5,024,671; U.S. Pat. No. 5,061,276; U.S. Pat. No. 5,116,360; U.S. Pat. No. 5,133,742; U.S. Pat. No. 5,152,782; U.S. Pat. No. 5,192,310; U.S. Pat. No. 5,229,431; U.S. Pat. No. 5,354,329; U.S. Pat. No. 5,453,235; U.S. Pat. No. 5,527,353; U.S. Pat. No. 5,556,426; U.S. Pat. No. 5,607,478; U.S. Pat. No. 5,609,624; U.S. Pat. No. 5,620,763; U.S. Pat. No. 5,628,782; U.S. Pat. No. 5,641,373; U.S. Pat. No. 5,665,114; U.S. Pat. No. 5,700,287; U.S. Pat. No. 5,716,395; U.S. Pat. No. 5,716,660; U.S. Pat. No. 5,800,510; U.S. Pat. No. 5,800,512; U.S. Pat. No. 5,824,050; U.S. Pat. No. 5,840,240; U.S. Pat. No. 5,843,173; U.S. Pat. No. 5,851,229; U.S. Pat. No. 5,851,230; U.S. Pat. No. 5,866,217; U.S. Pat. No. 5,897,587; U.S. Pat. No. 5,904,967; U.S. Pat. No. 5,910,168; U.S. Pat. No. 5,931,865; U.S. Pat. No. 5,976,192; U.S. Pat. No. 6,001,125; U.S. Pat. No. 6,036,724; U.S. Pat. No. 6,039,755 U.S. Pat. No. 6,042,666; U.S. Pat. No. 6,056,970; U.S. Pat. No. 6,080,198; U.S. Pat. No. 6,099,557; U.S. Pat. No. 6,203,735 U.S. Pat. No. 6,261,257; U.S. Pat. No. 6,267,834; U.S. Pat. No. 6,287,337; U.S. Pat. No. 6,319,279; U.S. Pat. No. 6,368,347; U.S. Pat. No. 6,416,537; U.S. Pat. No. 6,428,571; U.S. Pat. No. 6,534,084; U.S. Pat. No. 6,547,820; U.S. Pat. No. 6,589,468; U.S. Pat. No. 6,712,919; U.S. Pat. No. 6,716,239; U.S. Pat. No. 6,719,783; U.S. Pat. No. 6,790,226 U.S. Pat. No. 6,814,753; U.S. Pat. No. 6,827,737; U.S. Pat. No. 6,863,686; U.S. Pat. No. 6,926,735; and U.S. Publication Number (USpN) 2003/0004559; USpN 2003/0027775; USpN 2003/0100859; USpN 2003/0139806; USpN 2004/0033364; USpN 2004/0049264; USpN 2004/0054406; USpN 2004/0122507; USpN 2004/0182511; USpN 2004/0193242; and USpN 2004/0215337, each of which is incorporated by reference as if fully set forth herein.

Before accessing an ePTFE AV graft for hemodialysis, a blood flow check through the graft is normally conducted by feeling the pulse through the graft by gently touching the surface of the skin. The ability to feel the pulse through the graft is generally defined as "palpability." Most commercial ePTFE vascular grafts provide good palpability; however, when a layer of elastomeric sealant is placed on the surface of an ePTFE substrate, the palpability of the graft may be compromised if the layer is too thick. Another potential drawback in using ePTFE AV grafts for hemodialysis is that when implanted, there may be a tendency for the graft to form a kink at the loop site. Examples of a typical loop site is shown in FIGS. 1A (forearm loop AV graft 2, from the brachial artery to the basilic vein) and 1B (thigh loop AV graft 4, from the femoral artery to the femoral vein). Kinking of the graft at the loop site may occlude blood flow, in which case immediate medical intervention would be required. Clearly, such intervention is strongly disfavored as the likelihood of adverse outcomes are increased. Unfortunately, it has been discovered that ePTFE grafts coated with elastomeric sealant or otherwise formed to address the problem of sealing can easily form kinks, presumably due to the stiffness of the graft at the loop region.

One other potential drawback in utilizing ePTFE material is that it is radially non-compliant compared to a native blood vessel, meaning that the wave propagation of blood, which causes a native blood vessel to expand and contract as pulses of blood flow therethrough, dissipates as it travels through a ePTFE graft. This dissipation of the pulse can lead to various complications, such as compliance mismatch with respect to the host vessel. Unfortunately, to date, it is believed that a radially compliant ePTFE graft that mimics the compliance of a native blood vessel has not been successfully developed. Therefore, there is a need for a self-sealing ePTFE graft that overcomes some or all of the above-mentioned disadvantages.

BRIEF SUMMARY OF THE INVENTION

Accordingly, vascular grafts, and in particular ePTFE grafts and ePTFE AV grafts providing advantageous properties are described herein. In one aspect of the invention, a self-sealing vascular graft includes a generally tubular ePTFE substrate having a first surface and a second surface spaced from the first surface, wherein the ePTFE substrate is selected from the group consisting of a high porosity graft, a thin-wall graft and combinations thereof, and a layer of sealant disposed over one of the first and second surfaces of the substrate. In another aspect of the invention, a self-sealing graft includes a tubular ePTFE substrate, wherein the ePTFE substrate is either a high-porosity graft, a thin-wall graft or a combination thereof, and a layer of sealant disposed over at least a portion of the substrate. In yet another aspect of the invention, a graft for implantation as an AV fistula includes a tubular ePTFE substrate and a layer of sealant disposed over at least a portion of the substrate, wherein the sealant layer has a plurality of grooved sections spaced apart along the length thereof.

In another aspect of the invention, a vascular graft includes an outer polymer sealant layer surrounding a substrate and a base layer, and a plurality of foam layers dispersed between the substrate and the outer polymer layer. According to an alternative aspect of the invention, a vascular graft includes an inner sealant layer of polymer having a first thickness and surrounding a substrate; and a foam layer of polyurethane surrounding the inner sealant layer, the foam layer having a second thickness greater than 1.5 times the first thickness. In still another aspect of the invention, a vascular graft includes a substrate, including an outer wall, a base sealant layer, comprising a polymer sealant material, disposed over a length of the substrate, a first foam layer, comprising a polymer foam material, disposed over a length of the base layer, a beading embedded at least partially in the first foam layer, a second foam layer, comprising a polymer foam material, disposed over a length of the first foam layer and beading, and an outer layer, comprising a polymer.

In an alternative aspect of the invention, a method of forming a radially compliant graft includes providing an ePTFE substrate, radially dilating the substrate, disposing a layer of elastomeric material over the radially dilated substrate to provide a coated substrate, and heating the coated substrate. In another aspect of the invention, a method of forming a vascular graft includes providing an ePTFE substrate, applying a first layer of polyurethane over a length of the substrate, longitudinally compressing the substrate, applying a second layer of polyurethane over the first layer of polyurethane, wrapping a layer of ePTFE tape around the polyurethane coated substrate, the ePTFE tape passing first through a solution such that an amount of solution is applied to the ePTFE tape. In yet another aspect of the invention, a method of making a self-sealing vascular cuff graft includes positioning a neck portion of a cuff over a first end of an ePTFE substrate, dipping the substrate into a sealant material from a second end thereof to the neck portion of the cuff, and dipping the substrate and neck portion of the cuff in the sealant material. In still another aspect of the invention, a method of making a kink resistant self-sealing vascular graft includes providing a generally tubular ePTFE substrate, disposing a layer of sealant over at least a portion of an outer surface of the substrate, and creating grooved sections in the sealant layer.

In a further aspect of the invention, a self-sealing vascular graft includes a generally tubular ePTFE substrate having a first surface and a second surface spaced from the first surface, and a layer of sealant disposed over one of the first and second surfaces, the sealant comprising a polymeric material resistant to plastic deformation upon insertion of a puncture member through the sealant layer. In another aspect of the invention, a self-sealing vascular graft includes a generally tubular ePTFE substrate, a layer of sealant disposed over at least a portion of the substrate, and a beading disposed about a surface of one of the substrate and sealant.

In yet another aspect of the invention, a method of making a kink resistant self-sealing vascular graft includes providing a generally tubular ePTFE substrate, disposing a layer of sealant over at least a portion of an outer surface of the substrate, positioning a beading over at least a portion of the sealant layer, and coupling a cuff graft to the vascular graft. In another aspect of the invention, a method of making a self-sealing vascular cuff graft includes attaching a beading disposed generally helically about a substantially tubular ePTFE substrate having a first end and a second end extending along a longitudinal axis, coupling a flared vascular cuff to one of the first and second ends, and bonding the coupled vascular cuff and generally tubular ePTFE substrate. In a further aspect of the invention, a method of making a self-sealing vascular graft includes providing an elastomeric sealant layer over a length of an outer surface of an ePTFE substrate, and disposing a foam layer over at least a portion of the sealant layer, wherein a thickness of the foam layer is substantially greater than a thickness of a wall of the substrate. According to another alternative aspect of the invention, a method of making a self-sealing vascular graft includes dispensing at least one layer of polyurethane material onto a surface of an ePTFE substrate, and bonding an ePTFE member to the polyurethane material by applying a solvent to the ePTFE member.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIG. 2 is an illustration of an ePTFE graft having an ePTFE substrate with a sealant layer on either side of a middle portion, which has beading spiraled therearound.

FIG. 3 is an illustration of the graft of FIG. 2 with a foam layer disposed over the sealant layer and beading.

FIG. 4 is an illustration of the graft of FIG. 3 with an ePTFE tape wrapped around the foam layer.

DETAILED DESCRIPTION OF THE PREFERRED EMBODIMENTS

Figure 1:
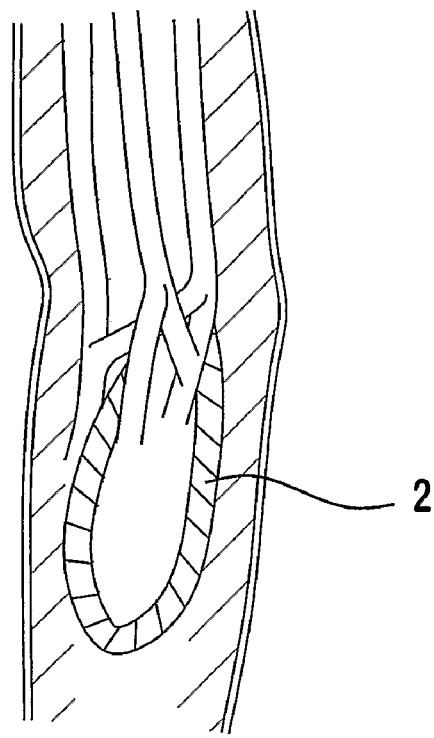
FIG. 1A is a depiction of loop AV graft implanted in the forearm of a patient.
FIG. 1B is a depiction of loop AV graft implanted in the thigh of a patient.
Figure 1:
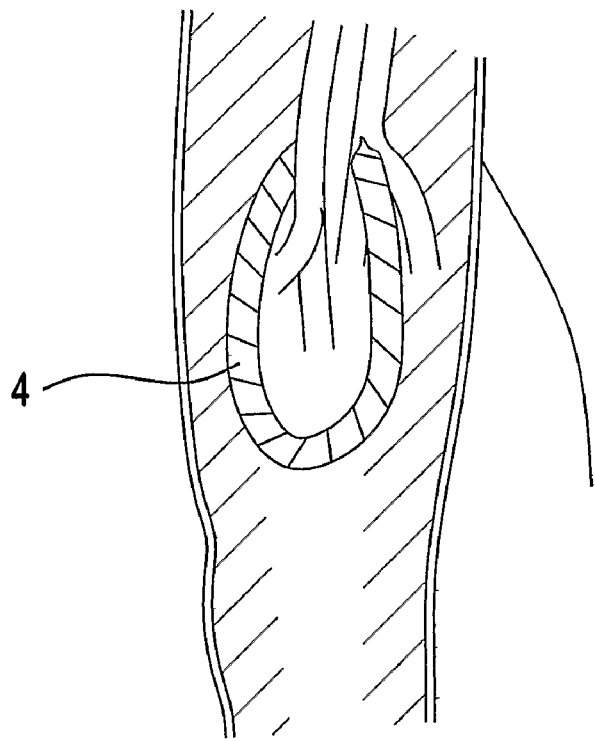

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

The examples contained herein utilize an ePTFE substrate. As is known in the art, an ePTFE substrate may be manufactured in a number of ways, including, for example, extrusion of a tube (seamless), extrusion of a sheet that is subsequently formed into a tube (one or more seams), helical wrapping of ePTFE tape around a mandrel (e.g., multiple seams or preferably a single helical seam), etc. While the preferred method used for forming an ePTFE substrate in the present invention is to extrude a tube, it should be appreciated that other forming methods are possible and are within the scope of the invention. Moreover, while ePTFE is discussed as being the material of choice for the substrate layer, one skilled in the art would appreciate that other materials are also suitable for use as a substrate, including, for example, polyester, polyurethane and fluoropolymers, such as perfluoroelastomers and the like.

Further, while the self-sealing properties of the grafts described herein are made with reference to blood loss due to removal of a needle therefrom, it should be appreciated that the self-sealing properties extend to blood loss resulting from suture holes created in the graft during implantation. Further still, it should be appreciated that the discussion of specific polyurethane materials herein with respect to a sealant layer are exemplary only and should not be utilized to limit the invention. In particular, many different types of polyurethane materials are within the scope of the invention, as are non-polyurethane elastomeric sealant materials. As used herein, the terms elastomer, elastomeric, sealant, and the like are used interchangeably to refer to a layer or layers of generally flexible material dispensed or disposed on a substrate that can, in most instances, impart sealing properties thereto but is not required to self-seal upon puncture.

In addition, bioactive agents may be incorporated into the material (or materials) forming the vascular grafts described herein. Bioactive agents can be incorporated with a synthetic non-metallic material (e.g., DACRON®, polyester, PTFE, ePTFE, polyurethane, polyurethane-urea, siloxane, and combinations thereof) in at least one of the luminal and abluminal surfaces of the grafts; dispersed throughout the synthetic non-metallic material of the grafts; coated thereon; spray-coated thereon; grafts dipped therein; vapor deposited thereon; sputter-deposited thereon; or used to form radio-opaque surfaces on the grafts. The material or combinations of materials used (e.g., DACRON®, polyester, PTFE, ePTFE, polyurethane, polyurethane-urea, siloxane, and combinations thereof) can include surface modifying additives or other materials.

It should be emphasized that variations in the configuration or composition of the substrate, bioactive agents, sealant layers, foam layers, other layers and other design parameters are to be utilized with the graft described herein. For example, the weight percentage of a bioactive agent in the graft can vary from about 0.1 percent to about 90 percent, and most preferably from about 10 to about 60 percent; the average particle size of the bioactive agent may range from about 20 nanometers to about 100 microns, and most preferably from about 0.1 micron to about 5 microns; the bioactive agent particle may be porous in certain configurations and non-porous in other configurations; bioactive agents may constitute 100 percent of the luminal or abluminal surface of the graft and can be homogeneously distributed throughout the entire graft body; bioactive agents may also constitute an adhesive film of about 10 microns to about 1000 microns.

Bioactive agents may include, but are not limited to, compounds such as carbon particles, silver particles, graphite particles, antibiotics (amethoprinrifampin or gentamycin); macrolide antibiotics; steroidal or anti-inflammation agents (e.g., estradiol); antineoplastic agents; antifungals; antivirals; antibodies; genetic sequence agents; growth factors inhibitors; angiogenesis; anti-angiogenesis; proteinase inhibitors; antiproliferative compounds or cell cycle modulators (such as rapamycin, sirolimus, or paclitaxel. These agents may be coupled with other agents, such as hydroxyapatite (HA), or other bio-compatible calcium salts, including, but not limited to dicalcium phosphate, tricalcium phosphate, tetracalcium phosphate, and other compounds in the calcium phosphate or calcium carbonate family. Any of the member of the family of calcium salts described can be utilized as long as the salt is not substantially osteo-inductive (i.e., bone forming) in the graft. Also, ceramic materials such as nano-sized carbon tubes, calcium carbonate, and genetic or viral materials may also be combined with at least one of the graft materials described herein.

With respect to utilization of HA or other bio-compatible calcium salts, various methods or techniques known to those skilled in the art can be used to incorporate drugs or bioactive compounds therein. For example, drugs may be added after a HA-graft composite is made. Organic or aqueous solvent based techniques can be used to diffuse the drugs or other bioactive agents into the HA particles. Alternatively, HA particles may be first loaded with drugs or other bioactive agents and then incorporated in the graft. The drug or other bioactive agent may be released quickly within 60 minutes or can be released in a controlled manner from few days to two years. Additional polymeric coating or ceramic coating on HA particles may be used to control the release of the drug or other bioactive agent.

Additionally, where ePTFE is used in conjunction with HA, the composite HA-ePTFE grafts may have different porosities and node-fibril structures. Porosity of the ePTFE may be in the range of about 5 microns to about 100 microns, with the preferred porosity or internodal distance ranging from about 10 microns to about 40 microns. By controlling expansion ratios, lubricant levels, PTFE resin particle size and other ePTFE processing parameters, grafts with various porosities can be made to provide HA coupled grafts with regions of different porosities. The HA coupled graft may also be made using multiple layers of ePTFE graft tubes. The HA based grafts may also have additional features described herein, such as a cuff or cuffs to improve patency, beading to improve kink resistance, and visible orientation lines to assist during implantation or other surgical procedures. These and other aspects of grafts incorporating HA or other bio-compatible calcium salts are described in U.S. Provisional Application No. 60/689,034, filed Jun. 8, 2005, entitled "Grafts and stent grafts having inorganic bio-compatible calcium salt," which is incorporated by reference as if fully set forth herein.

Sealant Layer

In one preferred embodiment of a self-sealing graft, the sealant layer material utilized is one that is believed to exhibit a low degree of creep or stress relaxation. Creep or stress relaxation of a material occurs due to plastic deformation thereof, which in the context of the preferred embodiments may occur due to the insertion of a needle through the material for an extended length of time. Examples of suitable materials for the sealant layer include, but are not limited to, aromatic polycarbonate polyurethanes, polyetherurethanes, polyether/polyamide block copolymers, polydimethylsiloxane elastomers, other silicone elastomers, etc.

With particular respect to the types of polyurethanes that exhibit a low degree of creep or stress relaxation, it has been demonstrated by experimentation that aromatic polyurethanes provide better resistance to plastic deformation than aliphatic polyurethanes. This can be explained, in part, by examining these compounds in more detail. Polyurethanes used in biomedical applications are generally synthesized in a two step process. First, a polymeric diol is reacted with a diisocyanate compound to form a pre-polymer with isocyanate end groups. The pre-polymer is then chain extended using a small molecular weight diol or diamine to form a polyurethane or polyurethane urea (reaction with amine). By choosing different types of polymeric diols, diisocyanates and chain extenders, many types of polyurethanes can be made with different properties. Among these, polyurethanes made using polycarbonate diol (polycarbonate polyurethanes) are used in many medical device applications due to their biostability upon implantation and excellent mechanical properties. The components of two commercially available polycarbonate polyurethanes are described below in Table 1 (listed as polymer X and polymer Y), the structural difference between the two being the diisocyanate used in the polyurethane synthesis:

TABLE 1

| Polymer | Polymer Diol | Diisocyanate | Chain Extender |
|---------|--------------|--------------|----------------|
| X | Polycarbonate diol | Dicyclohexylmethane-4,4-diisocyanate (aliphatic diisocyanate) | 1,4 butane diol |
| Y | Polycarbonate diol | Methylenebisphenyl diisocyanate (aromatic diisocyanate) | 1,4 butane diol |

Experimentation using the two polymers on different grafts was conducted first by flowing fluid through the graft, inserting a needle through the polymer sealant layer on respective grafts, maintaining the position of the needle through the polymer for approximately two hours, and removing the needle. The hole created in the polymer Y sealant layer substantially closed upon removal, while the hole created in the polymer X sealant layer remained substantially open upon removal. In a second experiment, both holes closed immediately upon removal of a needle that was only maintained in position for approximately two minutes. In a third experiment, grafts coated with polymer X and polymer Y were subjected to a fluid loss test, which simulated a dialysis session. A 14 gauge needle was inserted into the respective grafts and was maintained in position for one hour at 37° C. Upon removal of the needle, the graft coated with polymer X lost approximately 120 grams of fluid, while the graft coated with polymer Y lost approximately 15 grams of fluid. Thus, from this one experiment, it appears that polyurethanes prepared using aromatic diisocyanate exhibit superior sealing response compared to polyurethanes prepared using aliphatic diisocyanate for longer needle dwell times.

Further, the sealing response of the sealant layer may be improved through manipulation of the polymer by heating, which results in the lowering of the creep or stress relaxation exhibited by the sealant layer. This favorable response may be attributed to better phase separation of the soft phase (polycarbonate segments) from the hard phase (aromatic polyurethane segments) as heating develops an ordered domain for elastomeric properties (alignment of H bonds). In Table 2 below, grafts coated with polymer Y from Table 1 were subjected to various heat treatment procedures and tested for fluid loss. The resulting data indicates that certain heat treatments impart superior sealing response to polyurethanes, such as polymer Y, although heat treatments for longer periods of time resulted in a reduction in the sealing response of the graft due, at least in part, to the fact that the polyurethane began to dissolve. The best sealing response (i.e., least amount of fluid loss) with respect to heat treating polymer Y occurred when the polyurethane was heated for 4 hours at 70° C. It is understood that heat treatments may be different for other sealant materials.

TABLE 2

| Heat Treatment (polymer Y) | Average Fluid Loss (grams) ± Standard Deviation (needle dwell time) |
|---|---|
| No heat treatment - aged for 12 hours at 27° C. | 43 ± 17 (1 hour) |
| Heated for 12 hours at 70° C. | 18 ± 4 (1 hour) |
| Heated for 4 hours at 70° C. | 16 ± 6 (2 hours) |
| Heated for 12 hours at 70° C. | 29 ± 13 (2 hours) |
| Heated for 4 hours at 120° C. | 36 ± 3 (2 hours) |
| Heated for 12 hours at 120° C. | 33 ± 7 (2 hours) |

The sealing response of the sealant layer may also be improved by adding particles including polyethylene terephthalate (polyester) to the sealant material. In one example, polyester beads were ground and sieved to produce particles having a virtual average diameter of less than approximately 75 microns. The term "virtual average diameter" as used herein means an imaginary diameter d, generated by solving the following equation with a known cross-sectional area A of the particle (regardless of whether the cross-sectional area A is a square, rectangle, triangle, etc.): $A=\pi*(d/2*d/2)$. These particles were then added to a polymer, such as polymer X in Table 1 above, that was first dissolved in a suitable solvent such as, for example, an aprotic solvent including dimethylacetamide (DMSE), dimethylforamide, or tetrahydrofuran (THF). The polymer bead solution/dispersion was then applied to an ePTFE substrate and the solvent was removed by heating the graft (e.g., 70° C. for 10 minutes). Additional coats were applied to the ePTFE substrate to achieve a thickness of approximately 50-300 microns, and the graft was dried in a vacuum (e.g., 70° C. for 10-16 hours). When compared with a control graft that did not include the polyester particles, the experimental graft exhibited shorter coagulation time, indicating that the polyester surface in contact with blood promotes hemostasis that then assists with the sealant response after dialysis (likely due to the highly thrombogenic properties of polyester). Other materials that also could be used as particles to promote hemostasis include, but are not limited to, collagen, thrombin, fibrinogen and the like.

It is also noted that the thickness of the sealant will impact the sealing response of the graft, and that graft characteristics can be manipulated through the changing of the thickness of the sealant, which may be in addition to the processes/methods discussed above with respect to improving the sealing response of the graft (i.e., type of sealant chosen, heating processes, particle addition, etc.).

Self-Sealing ePTFE Graft

A self-sealing graft as described herein includes an ePTFE substrate with a sealant layer thereon, as described in U.S. Pat. No. 5,152,782 to Kowligi et al., which is commonly assigned and is incorporated by reference as if fully set forth herein. In particular, ePTFE substrates that are classified to one skilled in the art as either a high porosity graft or a thin-wall graft have been coated with a sealant layer and compared with a regular wall graft with a sealant layer, as well as the aforementioned types of grafts without a sealant layer. The term "high porosity graft" as used herein means a graft having an internodal distance (IND) in the range from approximately 30 to approximately 100 microns. The term "thin-wall graft" as used herein means a graft having a wall thickness less than approximately 500 microns, more preferably thickness ranging from approximately 200 to approximately 500 microns. By providing an ePTFE substrate that is either a thin wall graft or a high porosity graft (or a combination thereof), a sealant layer (e.g., elastomeric sealant such as polyurethane) disposed thereon such that it adequately penetrates into the wall of the ePTFE substrate will tend to dominate the closure response upon needle removal.

Experiment A below was conducted to show the advantage provided by a high porosity or thin-wall graft over a regular wall, regular porosity graft with respect to fluid loss after a needle is removed therefrom. While specific thicknesses and INDs are provided with respect to the tested grafts, it should be appreciated that additional ranges are possible that would be within the scope of this invention. Likewise, while a particular coating material and coating thicknesses are utilized, one skilled in the art would appreciate that varying the type of coating and the thickness of the coating on the graft is possible in order to maximize intended characteristics for desired applications and to maintain palpability of the graft, if desired. Finally, while a spray-coating process is described below, one skilled in the art will appreciate that there are many methods of coating a sealant layer on an ePTFE graft, including, for example, dip-coating, injection molding, co-extrusion, drape-coating, etc. (although it is noted that for grafts with complicated shapes (such as cuffs), spray-coating is presently preferred over dip-coating). Thus, the examples provided below are not meant to limit the scope of the invention in any way.

Experiment A

High porosity (HP) grafts were provided, along with regular wall (RW) grafts and thin-wall (TW) grafts, each having a length of 6 cm and a diameter of 6 mm. A 25% solution of BioSpan® segmented polyurethane (commercially available from Polymer Technology Group, Inc.) in dimethyl acetamide (DMAC) was diluted to 9-12% solution using DMAC. The diluted solution containing polyurethane (PU) was spray-coated on selected grafts (i.e., RWPU, TWPU and HPPU (see table 3)). The solvent was removed by heating the coated grafts at an oven air temperature of 70° C. for about 10 minutes. Additional coats were applied to achieve the final coating thickness. The coated grafts were then dried in a substantial vacuum at a temperature of 70° C. for about 10-16 hours. Control RW, TW and HP grafts without coating were also provided.

TABLE 3

| Polymer Code | Graft Description | Coating Thickness (microns) |
|---|---|---|
| Control RW | Regular wall (RW) graft, 700 microns thick, 10-20 microns IND. | N/A |
| Control TW | Thin wall (TW) graft, 400 microns thick, 10-20 microns IND | N/A |
| Control HP | High porosity (HP) graft, 700 microns thick, 45-85 microns IND | N/A |
| RWPU | RW graft coated with PU | 254 microns |
| TWPU | TW graft coated with PU | 341 microns |
| HPPU | HP graft coated with PU | 272 microns |

The self-sealing property of the vascular grafts was tested using a specialized apparatus that simulates internal blood pressure. A flow loop was created by circulating a fluid, such as one of about 40% glycerol/60% water mixture, but preferably water, through a flexible tube (about 6 mm in diameter, made of plastic, preferably silicone). The pressure in the flow loop was maintained by a peristaltic pump. The solution was heated to about 37° C. and circulated at about 600 ml/min. at approximately 1.9 psi pressure. A vascular graft was then connected to the flow loop and was punctured using a 16 gauge vascular access needle. Upon removal of the needle, the fluid seeping from the puncture site was collected for approximately 2 minutes and weighed. Each of the above listed grafts were tested and the fluid loss was recorded, the results of which are summarized in Table 4.

TABLE 4

| Polymer Code | Fluid Loss (grams) | Fluid Loss per mm Coating Thickness (grams) |
| --- | --- | --- |
| Control RW | 384.7 grams | N/A |
| Control TW | 198.9 grams | N/A |
| Control HP | 310.0 grams | N/A |
| RWPU | 24.7 grams | 97.2 grams |
| TWPU | 0.2 grams | 0.6 grams |
| HPPU | 3.1 grams | 11.4 grams |

It is clearly seen that the coated grafts provide significantly less fluid loss than the uncoated control grafts. The high fluid loss associated with uncoated grafts is attributed to the non-elastomeric nature of the PTFE thermoplastic. The needle puncture causes plastic deformation of the puncture site leaving behind a defect which permits fluid leakage. The coated grafts demonstrate self-seal upon needle puncture. This ability to self-seal is attributed to the elastomeric nature of the elastomer coated on the ePTFE outer surface. Among the coated grafts, the high porosity graft and thin-wall graft showed much better ability to self-seal than the regular wall graft. This may be attributed to the reduced contribution of the ePTFE material in dominating the properties of the puncture site. It should be noted that, as used herein, the term "about" or "approximately" for any numerical value denotes a suitable range of tolerance that would permit each of the preferred embodiments to function for its intended purpose as a self-sealing biological implant device.

With the thin-wall graft, reduced thickness of ePTFE permits the elastomer to dominate the punctured sealant site. This results in more efficient sealing and therefore reduced-fluid loss. With the high porosity graft, the higher porosity of ePTFE also permits the elastomer to dominate the punctured sealant site as upon coating, the pores in the surface of the graft are filled with the elastomer layer, which then dominate the properties of the sealing site. It has been found that an optimal thickness of an elastomer layer, and in particular a polyurethane layer, on a thin-wall and/or high porosity ePTFE graft is in the range of approximately 10-1500 microns. It has been discovered that a particular relationship in the preferred embodiments provide for a benefit not heretofore available. Specifically, it has been discovered that where the thickness of the ePTFE layer is less than the thickness of the polyurethane layer, the self-sealing property of the graft is enhanced. Furthermore, where the thickness of the ePTFE is about or less than 50% of a polyurethane foam layer (discussed below), the self-sealing property is tremendously enhanced.

The results obtained from Experiment A indicate that both a high porosity ePTFE graft and a thin-wall ePTFE graft are advantageous with respect to sealing properties upon coating with an elastomer layer. In addition, it was noted that the handling and feel of the high porosity coated graft was more pliable than the thin-wall and regular wall grafts. Thus, in a preferred embodiment, a self-sealing ePTFE graft is provided that has a substrate of a high porosity graft or a thin-wall graft, which substrate is coated with a layer of elastomeric material. In another preferred embodiment, a combination high porosity thin-wall ePTFE graft is provided with a coating of elastomeric material for a self-sealing ePTFE graft.

In another preferred embodiment, a dual graft is provided wherein an outer tubular ePTFE graft is coaxially positioned around an inner ePTFE graft This may be accomplished in many ways, one of which is co-extrusion. The outer ePTFE graft could be a thin-wall graft or a high porosity graft with an elastomeric sealant layer thereon. The inner ePTFE graft could be any type of ePTFE graft (e.g., regular wall graft, thin-wall graft, high porosity graft, etc.) with properties different than the outer ePTFE graft to complement any deficiencies in the outer ePTFE graft. For example, if the outer ePTFE graft was a high porosity ePTFE graft with a sealant layer, an inner ePTFE graft having a lower porosity may be utilized to act as a barrier to prevent sealant from becoming a blood contracting surface. Also, because lower porosity grafts are standard clinical grafts, the surface area and microstructure of the graft can be maintained while achieving the benefits of sealing on the outside of the graft. Notably, the combination of an outer high porosity ePTFE graft and an inner lower porosity graft was achieved through experimental testing by producing a single extrusion, dual graft with an inner high porosity ePTFE graft and an outer lower porosity ePTFE graft and inverting the dual graft. Alternatively, a single extrusion without inverting can be utilized.

In one embodiment, a dual porosity graft is made wherein a high porosity graft is initially positioned concentrically within a standard graft, having a typical porosity. A section of the graft is cut and then inverted so that the abluminal surface of the graft, which began as the standard graft becomes the luminal surface of the graft and vice versa. The inverted graft, now having the high porosity graft as the abluminal surface, is coated (on the abluminal surface) with polyurethane as described above. In yet another preferred embodiment, a graft having a thickness of about 260 microns with a polyurethane sealant layer of about 100 microns, a polyurethane foam layer of about 700 microns, and an outer ePTFE wrap from about 20 microns to about 150 microns is provided. The fluid loss for this embodiment as measured using the testing apparatus discussed above is about 73 grams or less.

A supplemental study was conducted to test suture hole bleeding for graft end conformability. The ePTFE graft utilized was characterized by a reduced wall thickness at the ends of the graft (200 microns). The graft was installed into a flow loop that pumped an approximate 40% glycerol/60% water mixture at approximately 600 ml/min with an internal pressure of about 2.2-2.5 psi and a liquid temperature of about 37° C. A #6 propylene suture was used to produce 3 punctures with the thread removed from the hole. The fluid loss collected in a tray for a total of 2 minutes. The fluid loss was then measured using a scale. The control graft was a bare ePTFE graft (no sealant, same thickness). The control graft lost about 2 grams of fluid per hole for the two minute test period, while the experimental graft with sealant, having a total wall thickness of about 300 microns, lost only about 0.13 grams per hole in the same period of time.

ePTFE AV Graft

The above examples of an ePTFE graft coated with a sealant are discussed in terms of advantageous self-sealing properties. However, use of a sealant layer on an ePTFE substrate may have the disadvantage of considerably lowering the kink resistance of the graft. Thus, the embodiments described above may be favored in the case that an ePTFE AV graft is implanted in such way that no bend in the graft is necessary. Where an ePTFE AV graft will require a bend for implantation (such as shown in the examples of FIGS. 1A and B), additional processing steps may be required to impart kink resistance to the graft.

A first example of a processing step to increase kink resistance in a coated ePTFE graft, which step also imparts longitudinal compliance to the graft, is a step of longitudinally compressing the ePTFE graft prior to the step of coating the ePTFE graft with a sealant, as shown and described in U.S. Pat. No. 4,995,899 to Della Coma et al., which is commonly assigned and is incorporated by reference as if fully set forth herein. Compression of the ePTFE graft can be accomplished, for example, by placing the ePTFE graft over a cylindrical mandrel and applying a compression force along its longitudinal axis. The compression of the ePTFE graft prior to coating acts to increase kink-resistance by allowing the graft to stretch on the outer diameter of the bend and compress on the inner diameter of the bend. For ePTFE AV grafts, the longitudinal compression of the ePTFE graft prior to coating with a sealant layer is generally utilized whether or not further processing steps are employed.

It should also be noted here that it has been discovered that radial compliance can be imparted to an ePTFE graft by radially dilating the ePTFE graft substrate prior to coating the graft with a layer of elastomeric material. In a preferred embodiment, prior to applying a layer of elastomeric material to an ePTFE substrate, the substrate is dilated to a dilated diameter in the range of about 1.5 times to about 5 times the original diameter of the substrate. In another preferred embodiment, prior to applying a layer of elastomeric material to an ePTFE substrate, the substrate is dilated to a dilated diameter in the range of about 4 times to about 5 times the original diameter of the substrate. When the internal radial force is removed (following application of the elastomeric material) and the graft is heated, the ePTFE coated graft will revert to about the original diameter thereof. Upon subsequent application of internal force and removal thereof, the ePTFE graft will revert such that radial compliance is imparted, mimicking a native blood vessel.

A second example of a processing step to increase kink resistance in a coated ePTFE graft is a step of wrapping a beading around the outer surface of the graft. Depending on the specifications of the coated ePTFE graft over which the beading will be disposed (e.g., material properties of graft, dimensions of graft, material properties of sealant, dimensions of sealant layer, intended use of the graft, intended placement location of the graft, etc.), a number of beading parameters are possible. For example, the thickness of the beading, the type of beading material, the hardness of the beading, the spacing between windings of the beading, the cross-sectional shape of the beading, and the winding angle of the beading can all be varied to achieve the intended performance of the ePTFE AV graft, and in particular the kink resistance thereof. Further, a radiopaque pigment can be incorporated into the beading to provide radiopacity for X-ray contrast. Examples of radiopaque materials to be incorporated into the beading include, but are not limited to, barium sulfate, bismuth subcarbonate, bismuth trioxide, tungsten, tantalum, etc. In one embodiment, the beading includes a metallic material exhibiting radiopacity. In Experiment B, summarized below, different beading parameters were tested for acceptable kink resistance.

Experiment B

A 6 mm ePTFE graft was provided. Approximately 12 grams Carbothane® PC-3585A was dissolved in approximately 88 grams dimethyl acetamide (DMAC) to prepare an approximately 12% solution. The polymer solution was then spray-coated using a Binks Model 2001 spray gun with a nozzle orifice diameter less than about 1 mm on the outside surface of the graft after the graft was first longitudinally compressed. The solvent was removed by heating the coated graft at an oven air temperature of about 70° C. for about 10 minutes. Additional coats were applied to achieve a coating having a thickness of about 50-300 microns. The coated graft was dried in a substantial vacuum at about 70° C. for about 1-16 hours. The exterior sealant surface of the coated graft was then sprayed with DMAC (for polyurethane sealant) to soften the polymer coat. It is noted here that in the case that a silicone based sealant is used for the outer sealant layer, a material such as P-Xylene can be used to soften the sealant layer.

A beading was then spiraled around the graft for radial support. While the beading can be provided with various materials, such as, for example, metal (e.g., superelastic metals, shape memory materials, stainless steel, etc.), polyester, nylon, polyurethane, PTFE, ePTFE, etc., the beading materials used in this experiment were ePTFE, Nitinol and polyester. After complete removal of solvent, the beading adhered to the sealant and was partially embedded in the sealant layer. It should be noted that for optimal adherence of the beading to the graft through simple processing steps (e.g., heat, pressure, etc.) without the use of solvents or adhesives, the portion of the graft over which the beading is spiraled should have the same or similar material in contact with the beading. Thus, if the section to be beaded has been coated with a polyurethane sealant, the beading should include a similar polyurethane material. Likewise, if the section to be beaded has not been coated (i.e., the contacting surface is ePTFE), the beading should include ePTFE.

A design of experiment (DOE) was performed and analyzed using commercially available software (e.g., Design Expert Software) to examine the response of kink resistance of an ePTFE coated graft with beading as produced according to the above method. Two factors were examined: the spacing of the beading (3 levels) and the material/size of the beading (5 levels). The spacing levels were 0.5 mm, 1.5 mm, and 2.5 mm. The material/size levels were ePTFE IMPRA standard beading (approximately 0.700 mm), ePTFE IMPRA small beading (approximately 0.400 mm), Nitinol wire (approximately 0.380 mm), ePTFE Davol beading (approximately 0.260 mm), and polyester beading (approximately 0.200 mm). The DOE consisted of 15 runs (3×5) using a response surface design. Kink radius was a single response and was measured using the following method. A series of varied sized (diameter) mandrels and/or disks are used to determine the radius (inches) in which a graft could be bent before developing a kink. The set of mandrels have a thickness of 1 inch and a diameter ranging from 1-8 inches. Experimental grafts are cut to a length of approximately 6 inches. The ends of the experimental graft are held by hand and slowly introduced longitudinally to the wall of the mandrel (angled surface). The graft is introduced to each size of mandrel in succession starting with the largest diameter and proceeding to the smallest diameter. The first mandrel that produces a kink response in the sample is recorded. The mandrel diameter is recorded as the graft's kink radius.

Using this method, values were recorded and input into the software; responses ranged from approximately 0.5 to approximately 3.5 inches. The statistical model was significant ($p=0.004$) for a response surface linear analysis. Spacing (Factor A, $p=0.0146$) and material/size (Factor B, $p=0.0055$) were significant model terms. The slope was the same for beading types as spacing increased with respect to kink radius. This indicated that the smaller spacing gave better kink resistance. The materials/sizes that performed best were Nitinol (approximately 0.380 mm) and ePTFE IMPRA standard beading (approximately 0.700 mm), having identical responses at each spacing level. The remaining three material/size levels performed in the following order of decreasing desirability: ePTFE IMPRA small beading (approximately 0.400 mm), ePTFE Davol beading (approximately 0.260 mm), and polyester beading (approximately 0.200 mm). The results would appear to indicate that hardness and large diameter play an important role in kink resistance. The other beading types, which were of 3 different sizes but of 2 similar materials with respect to hardness (ePTFE & polyester), performed in a manner that reflected greater kinking as diameter decreased. Using software modeling, it was shown that by further reducing spacing to approximately 0.1 mm, both Nitinol and ePTFE IMPRA standard beading could provide an even better kink radius of about 0.33 inch. It is noted here that further testing has shown that polyurethane elastomer beading with a hardness of greater than approximately 72 Shore D exhibits excellent kink resistance and can be easily joined to an elastomer sealant layer. It is also noted that the kink resistance can be improved by adding filler material to the polyurethane material. Further, the application of tension force onto the beading as the beading is wound onto the graft is believed to be at least as important as the bead spacing.

A third example of a processing step to increase kink resistance in a coated ePTFE graft is a step of selective deposition of sealant materials on the graft surface. Such selective deposition can be accomplished by sectioned laser ablation or otherwise grooving the sealant material at spaced apart intervals over at least a portion of the length of the coated ePTFE graft. The grooving can be accomplished through the use of a $CO_2$ laser or other instrument that is capable of cutting precision grooves through the sealant layer to the ePTFE substrate. The grooves can be cut into the sealant layer at any angle or depth and can be spaced apart at any length. Moreover, the angle of the grooves and/or the length between grooves can be varied along selected lengths. The grooving of the coated ePTFE graft as a processing step can be used either alone or in combination with the previously mentioned processing steps and/or any processing steps not specifically mentioned herein to increase kink resistance in a coated ePTFE graft. In addition, only selected lengths of the coated ePTFE graft may be grooved (e.g., a mid-portion of the coated ePTFE graft where the graft is to be bent upon implantation). In Experiment C, summarized below, a grooving processing step was performed on a coated ePTFE graft and the grooved graft was tested for kink resistance.

Experiment C

A polymer coated ePTFE graft was placed on a mandrel and was fixed between two chucks located on an automated rotary fixture. A graphic was designed using software that interfaces with a $CO_2$ laser and scans the laser beam to etch the graphic on a given surface. Laser parameters were set and upon actuation of the start sequence, the laser cut grooves into the sealant layer of the coated ePTFE graft. The laser beam was adjusted so that only grooves in the sealant layer were created such that the ePTFE surface was not affected by the laser. Several types of grooves were cut and evaluated for kink resistance. The results of this experiment appeared to be that the best kink resistance resulted when the distance between grooves was minimized (i.e., in the range of about 1 mm to about 5 mm) and/or the angle of the grooves through the surface of the sealant layer was in the range of approximately 80-90° relative to the axis of the graft (i.e., approximately perpendicular with respect thereto).

A fourth example of a processing step to increase kink resistance in a coated ePTFE graft is a step of placing a foam layer over the coated ePTFE graft. The foam can include a polymer material and may be disposed onto the outer surface of a coated ePTFE graft (which may have undergone any of the above-referenced processing steps either alone or in combination). While one skilled in the art should appreciate that there are numerous ways in which a polymer foam may be disposed onto the outer surface of a coated ePTFE graft, three examples are provided herein (including exemplary amounts of materials used) as follows:

1) Approximately 16 grams Bionate® polyurethane is dissolved in about 84 grams dimethyl acetamide and the solution is spray-coated onto a surface of a coated ePTFE graft, after which the entire graft is immediately dipped or placed in water (at room temperature) for about 30 minutes and then placed in about 40° C. water temperature for about 16 hours. The precipitated polyurethane foam is air-dried for about 24 hours thereafter.

2) In a salt leaching technique, sodium chloride is ground using mortar and pestle and sieved using a 300 mesh (75 microns) sieve. Approximately 2.5 grams Bionate® polyurethane, about 10 grams dimethyl acetamide and about 7.5 grams of sodium chloride are mixed in a 250 ml plastic beaker. The solution is stirred until complete dissolution of the polymer is achieved. The polymer solution-salt dispersion is then spray-coated on a surface of the graft. The solvent is removed by drying, the salt being removed by dipping or placing the graft in hot water (approximately 60° C.) for approximately 16 hours.

3) Approximately 12 grams tetrahydrofuran (THF) and about 88 grams Carbothane® polyurethane are mixed and stirred until a clear solution is obtained. The mixture is sprayed on the graft surface using a standard spraying apparatus. During the spraying, the THF evaporates, leaving polyurethane strands or elongated polyurethane particles wrapped around the graft surface, resulting in a porous foam-like substrate around the graft.

With respect to the aforementioned techniques, it should be appreciated that other polymers and compounds would be equally effective in creating a polymeric foam for deposition on an underlying ePTFE substrate. For instance, in another example of a salt leaching technique, a polymer, such as silicone or urethane, could be combined with a finely ground salt, such as sodium chloride, ammonium bicarbonate, and/or ammonium carbonate, such that the polymer is dissolved in a solution (but not the salt) to create a polymeric solution. This solution can then be sprayed or coated onto the substrate (which may have first been coated with a polymeric base layer) to create a matrix of salt and polymer. Further processing involves allowing the polymer solvents to evaporate and removing the salt by water leaching so that the pores are formed in the polymer matrix where the salt granules have dissolved. In the case that ammonium bicarbonate and/or ammonium carbonate are used, these salts can be removed without water by simply heating the graft slowly in an oven set at approximately 30° C. air temperature.

While a primary advantage to having an outer foam layer, in addition to providing kink resistance, is that the sealing response of the graft is enhanced, a further advantage is that it provides a favorable "feel" to the graft, which is true regardless of the configuration of the graft over which the foam is disposed (i.e., regardless of how many of the above processing steps have been employed). With particular respect to a coated ePTFE graft that has undergone grooving, the foam will enter the grooved sections and will provide assistance in sealing and impediment of fluid loss in those sections, as well as resistance to infection (by preventing blood accumulation in the grooves, which accumulation may have potential for bacterial contamination).

A coated ePTFE graft created using the above processing steps, either alone or in combination, may further be prepared for use as an ePTFE AV graft by wrapping with an outer layer of porous material, such as ePTFE tape. The addition of an outer wrap is believed to enhance tissue ingrowth into the ePTFE AV graft to anchor the graft within the body tissue and also to reduce tissue fluid exposure to the polyurethane layer(s). The thickness and density of the outer wrap can be selected so that kink resistance and handling are not negatively affected. With respect to adhering ePTFE tape to an underlying non-PTFE material, such as polyurethane, it has been discovered that concomitant use of a solvent, such as THF, acts to bond the ePTFE tape to the underlying material. The THF or other solvent can be applied to the ePTFE tape by spraying after the tape has been applied to the graft (i.e., helically wrapped) or by soaking the tape in the solvent prior to wrapping.

In a preferred embodiment, ePTFE tape is wrapped over a sealant layer, such as polyurethane, after first passing over or through a solvent dispensing apparatus. For example, a graft on a mandrel could be rotated as ePTFE tape is fed from a spool on a pulley system, the ePTFE tape passing over a dispensing apparatus positioned between the mandrel and pulley system. The dispensing apparatus could take on a variety of configurations, but in one embodiment is a pressurized tube with one or more apertures, slits or other openings therein connected to a reservoir containing the solvent to be dispensed, a pressure control device and a regulator. Positioned over the opening(s) on the dispensing tube is a sponge or similarly functioning article that becomes saturated with the solvent upon commencement of the procedure. As the ePTFE tape is fed from a spool on the pulley system to the graft on the mandrel, it passes over the dispensing tube sponge, such that an even amount of solvent is applied to the ePTFE tape.

Table 5 presents results obtained with respect to kink resistance and fluid loss when comparing a standard thin-wall ePTFE graft with ePTFE grafts having one or more of the above processing steps. The sealant utilized in those grafts having a sealant layer was Carbothane® PC-2585A, having a thickness of approximately 300 microns. The grooving was performed using a CO2 laser at approximately a 90° angle with respect to the graft with spacing at approximately 2 mm. The wrap was an ePTFE tape having a thickness of approximately 0.096 mm and a width of approximately 6 mm.

TABLE 5

| Graft Type | Kink Radius (in.) | Fluid loss (grams) Average of two punctures |
|---|---|---|
| Control | 0.5 in. | 384.7 grams |
| Sealant layer | 3.0 in. | 1.0 grams |
| Sealant layer grooved with foam layer | 1.5 in. | 29.5 grams |
| Sealant layer grooved with foam layer and wrap | 1.5 in. | 7.5 grams |

The results of Table 5 indicate that an ePTFE AV graft prepared utilizing a combination of the above mentioned processing steps, namely a grooved sealant layer with a foam layer and an outer wrap, provides much better kink resistance while maintaining nearly optimal sealing levels compared with a coated ePTFE graft without any of the aforementioned processing steps.

Experiment D

A combination of the above-identified processing steps may enhance the elastomeric ability and/or memory shape ability of a polymer. In particular, in one embodiment of the present invention, a polymer's self-sealing properties may be enhanced through longitudinal and/or radial compression, as the polyurethane layer(s) will recover more quickly to an original configuration following stress (e.g., removal of a needle inserted therethrough). Moreover, it should be appreciated that the processing steps described herein to create an ePTFE AV graft with different radial zones can also be utilized to create different longitudinal zones along the length of the graft, wherein, as with each radial zone, each longitudinal zone is optimally prepared to exhibit a specific characteristic or characteristics (e.g., suture retention strength, self-sealing properties, kink resistance, etc.).

In Experiment D, approximately 28 grams of a polyurethane were dissolved in approximately 372 grams of THF and the resulting solution was sprayed (using a Binks Model 2001 spray gun with a nozzle orifice diameter of less than about 1 mm) onto the surface of a rotating ePTFE substrate on a rotary fixture at a distance of approximately 2 inches. This first layer was added until the total wall thickness of the graft was approximately 50 microns. The spray gun was then moved away from the graft to a distance of approximately 30 inches and the solution was sprayed again onto the rotating surface of the graft, the distance imparting a foam structure to the polyurethane prior to reaching the graft surface. The polyurethane foam was added until the thickness of the resulting graft wall was approximately 1 mm. The graft was then placed into an oven set at approximately 100° C. air temperature for approximately 2 hours. The graft was then longitudinally compressed to approximately 80% of its original length (e.g., a graft having original length of 10 inches is compressed to 8 inches). While compressed, a polyurethane beading, as discussed above, was helically wrapped around the foam layer with a bead spacing of between approximately 2.5 mm and approximately 3.5 mm. Another layer of polyurethane foam was then applied over the beading, followed by an outer wrap of ePTFE tape, which was applied under compression to reduce the outside diameter of the graft from approximately 1.9 mm to approximately 1.2 mm. The resulting product was placed into an oven set at approximately 100° C. air temperature for approximately 1 hour to cure. Following the curing step, the graft was cut into four equal parts for testing.

The Experiment D grafts were compared to two different sets of grafts that were produced similarly, with the exception being that one set of grafts was not compressed longitudinally (but was compressed radially) and the second set was not compressed either longitudinally or radially. The grafts were attached to a cannulation fixture comprising a water flow loop with an internal pressure from about 1 psi to about 2 psi and a fluid flow of about 600 ml/min. A 14 gauge needle was inserted through the wall of each graft and maintained in position for either 1, 2, 3, or 4 hours of dwell time. For like dwell times, average fluid loss through the non-compressed set of grafts was greater than that of the radially compressed set of grafts, which in turn was greater than that of the Experiment D grafts, indicating that compression in both longitudinal and radial directions in the manner described imparts to polyurethane layer(s) enhanced self-sealing properties.

Figure 5:
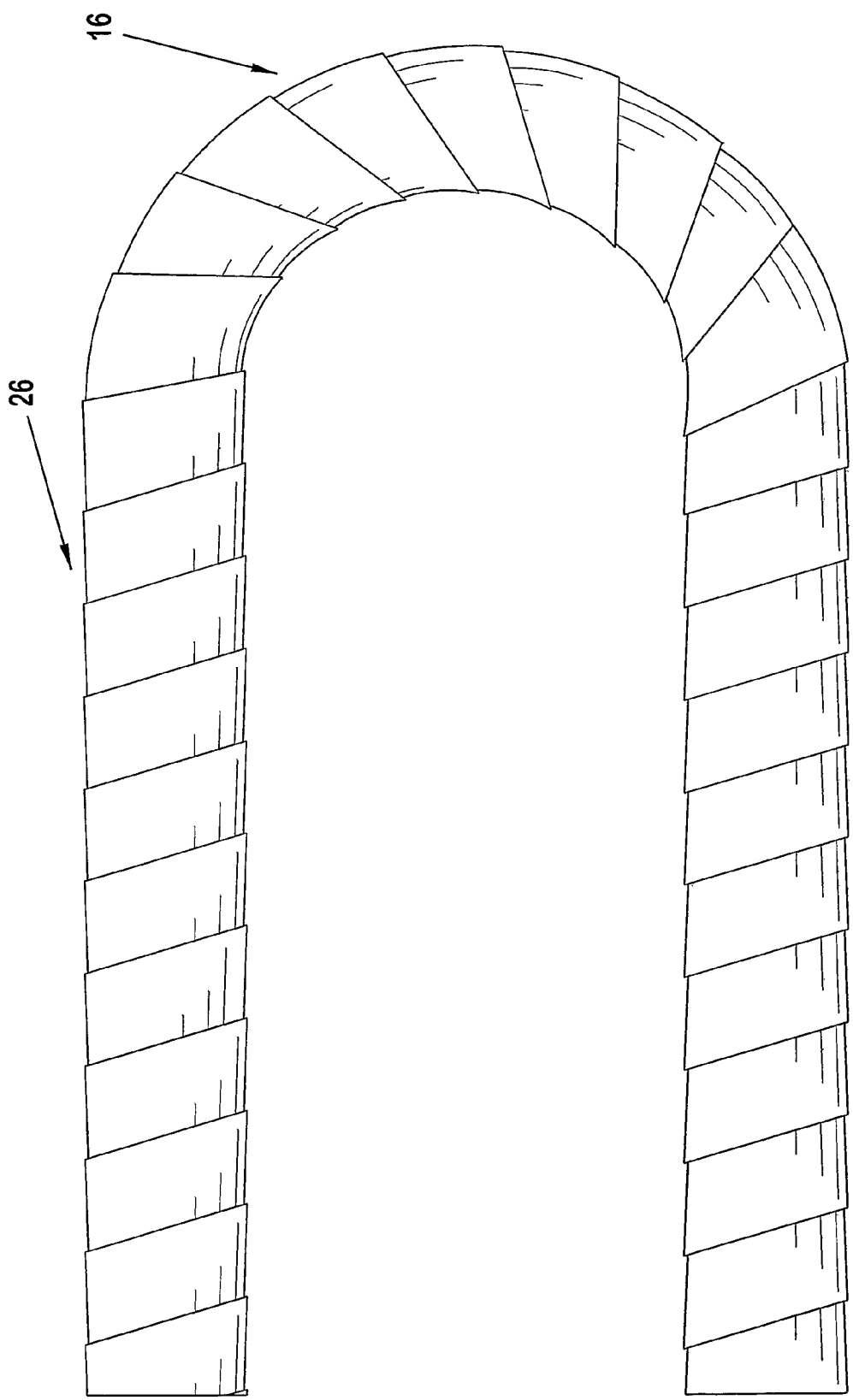
FIG. 5 is an illustration of the graft of FIG. 4 shown in a bent configuration.
Figure 6:
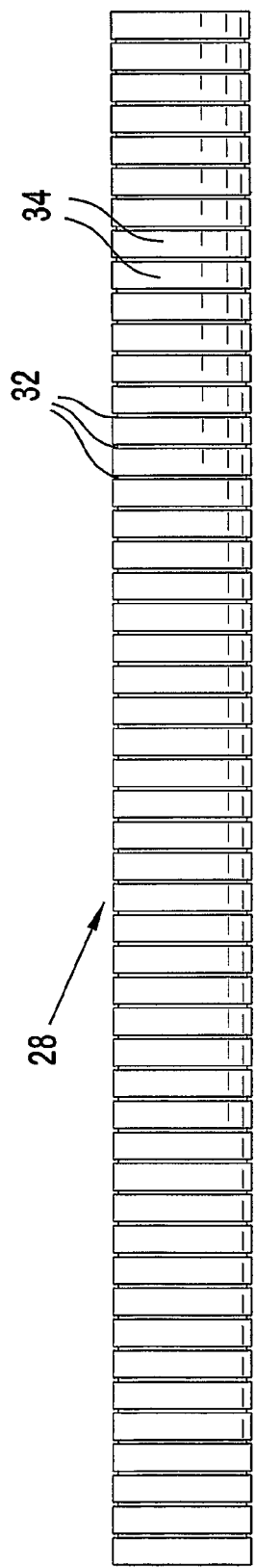
FIG. 6 is an illustration of an ePTFE graft having an ePTFE substrate with a sealant layer over its length, the sealant layer having grooved sections cut in spaced apart intervals therein.
Figure 7:
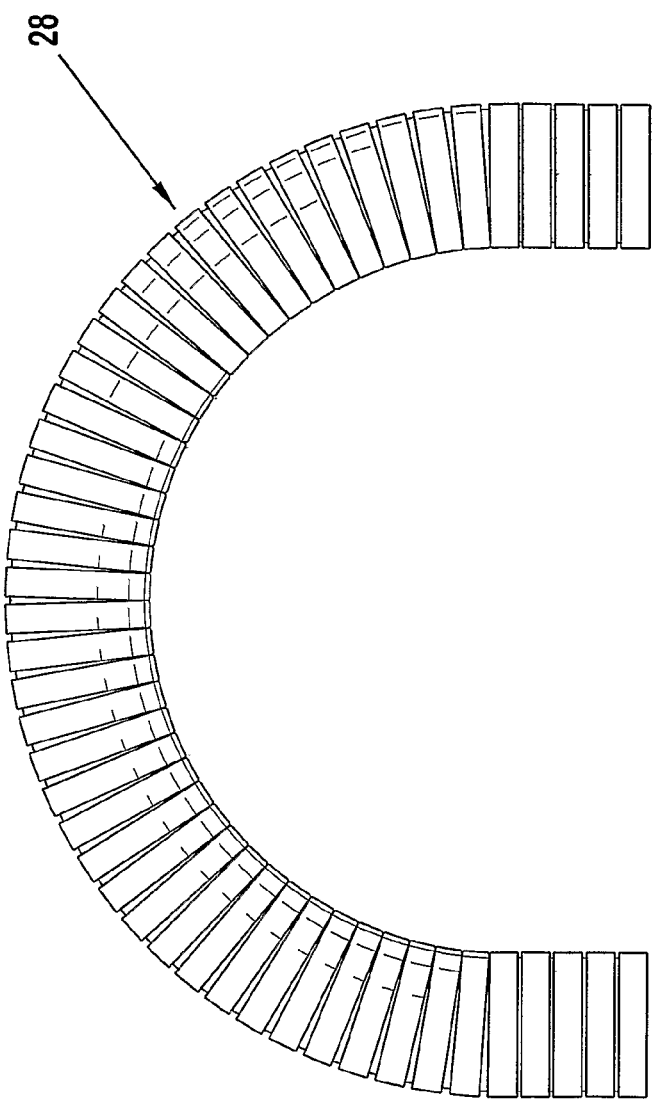
FIG. 7 is an illustration of the graft of FIG. 6 shown in a bent configuration.
Figure 8:
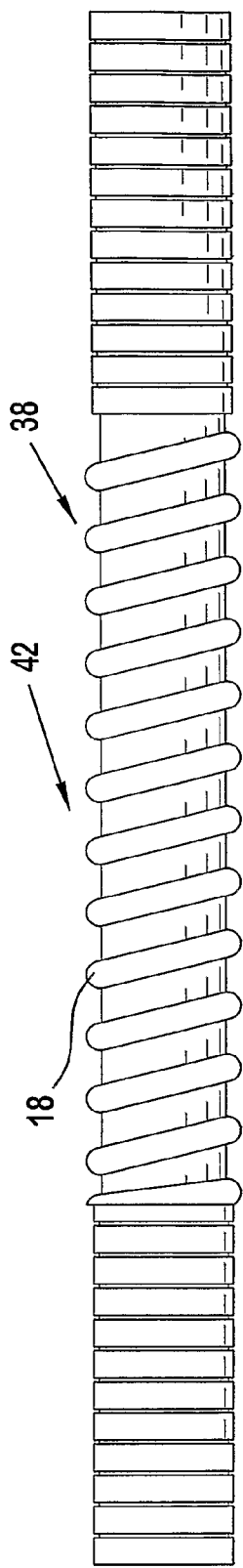
FIG. 8 is an illustration of an ePTFE graft having an ePTFE substrate with a sealant layer on either side of a middle portion, which has beading spiraled therearound, the sealant layer having grooved sections cut in spaced apart intervals therein.
Figure 9:
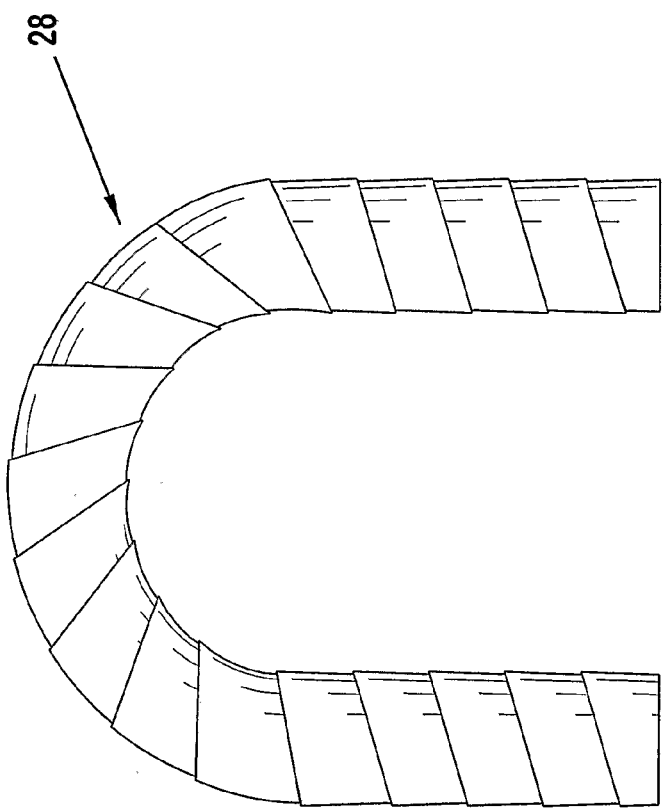
FIG. 9 is an illustration of the graft of FIG. 8 with a foam layer disposed over the sealant layer and beading, shown in a bent configuration.

FIGS. 2-9 are illustrations of coated ePTFE grafts incorporating one or more of the above-identified processing steps. FIG. 2 shows an ePTFE substrate 12 having a polyurethane coating 14 over portions of its length leading up to a middle portion 16, but not including the middle portion 16, which has a helically wrapped PTFE beading 18 disposed thereon. FIG. 3 shows a polymer foam layer 22 over the ePTFE graft of FIG. 2, while FIG. 4 shows an outer wrap of ePTFE tape layer 24 helically wound about the foam layer 22 of FIG. 3 to create an ePTFE AV graft 26. FIG. 5 shows the graft 26 of FIG. 4 in a looped configuration (i.e., bent along middle portion 16), exhibiting excellent kink resistance at a very small radius. FIG. 6 shows a graft 28 including an ePTFE substrate having a polyurethane coating over its entire length, the coating having grooves 32 cut therein at an angle approximately perpendicular to the longitudinal axis of the graft. The graft 28 also has a pair of parallel orientation lines extending longitudinally along a length thereof. FIG. 7 shows the graft 28 of FIG. 6 in a looped configuration to demonstrate the kink resistance provided by the grooves 32. FIG. 8 shows a graft 38, similar to graft 28, but without any sealant layer on a middle portion 42, which instead includes a helically wrapped PTFE beading 18 (as in FIG. 2). FIG. 9 shows graft 38 with a foam layer and an outer wrap of ePTFE tape helically wound about the foam layer, the graft 38 shown in a looped configuration, also exhibiting excellent kink resistance at a very small radius.

Figure 10:
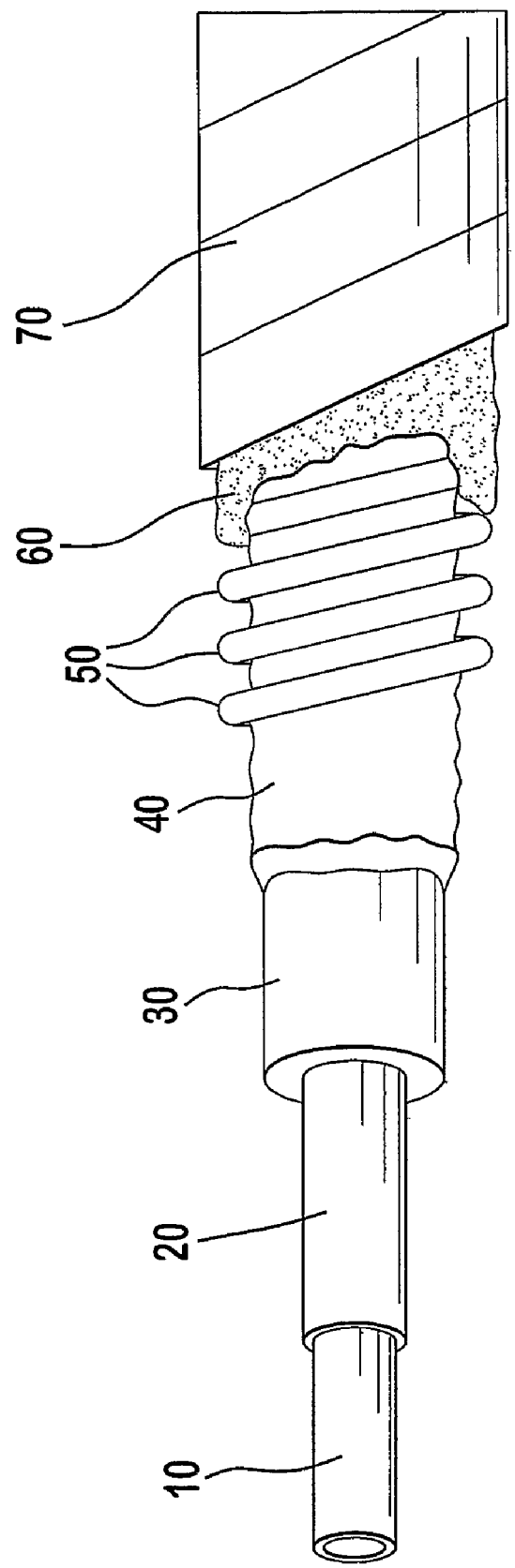
FIG. 10 is an illustration of an ePTFE AV graft according to the present invention with multiple layers of material.

FIG. 10 illustrates different layers of material for an ePTFE AV graft as described herein. It should be appreciated that the disposition of the layers in FIG. 10 is to exemplify the different types of layers and does not necessarily reflect the order of the layers with respect to one another. An ePTFE tubular substrate 10, which may include a thin-wall graft or high porosity graft as discussed above, is surrounded by a polyurethane base coat 20. This base coat 20, which in one embodiment is disposed over the entire length of the ePTFE substrate 10, may be made of a material such as polyurethane. A portion of the base coat will penetrate the wall of the graft. A sealant layer 30 is disposed over the base coat 20 and also may be made of polyurethane (or other types of materials, as discussed above), having a thickness which is dependent on various factors such as graft wall thickness, sealant type, etc. Generally, however, the thickness of the sealant layer and base coat will be in the range of approximately 10-400 microns, preferably about 20 microns to about 40 microns for the base coat 20, and about 100 microns total for the sealant layer and base coat. The sealant layer 30 may be disposed over the entire length of the graft, but in one embodiment is not positioned over either the ends of the graft nor in a middle portion of the graft. As discussed above, the sealant layer 30 may be grooved along selected lengths of the graft to aid in kink resistance. Positioned over the sealant layer 30 is a foam layer 40, followed by a beading layer 50, another foam layer 60 and an outer wrap layer 70.

Figure 11:
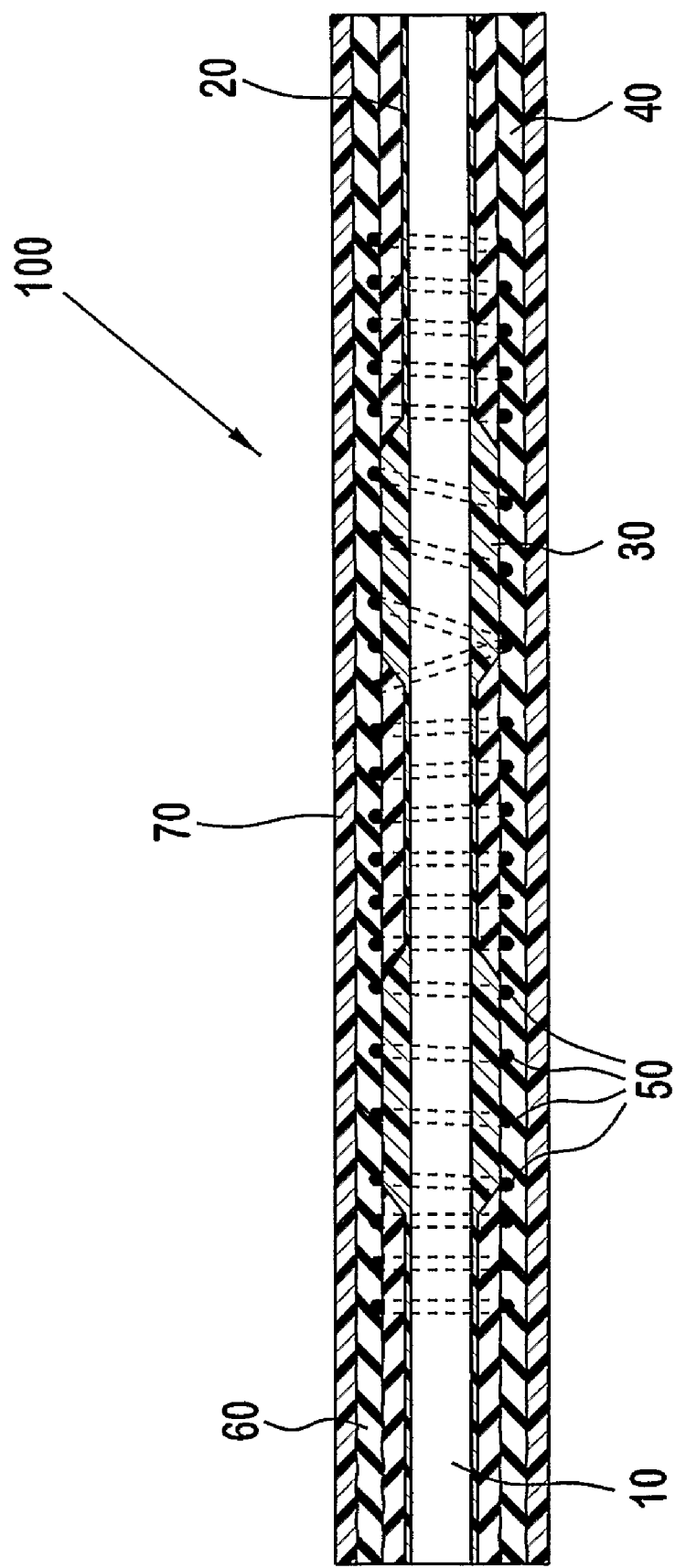
FIG. 11 is an illustration of one embodiment of an ePTFE AV graft according to the present invention.
Figure 12:
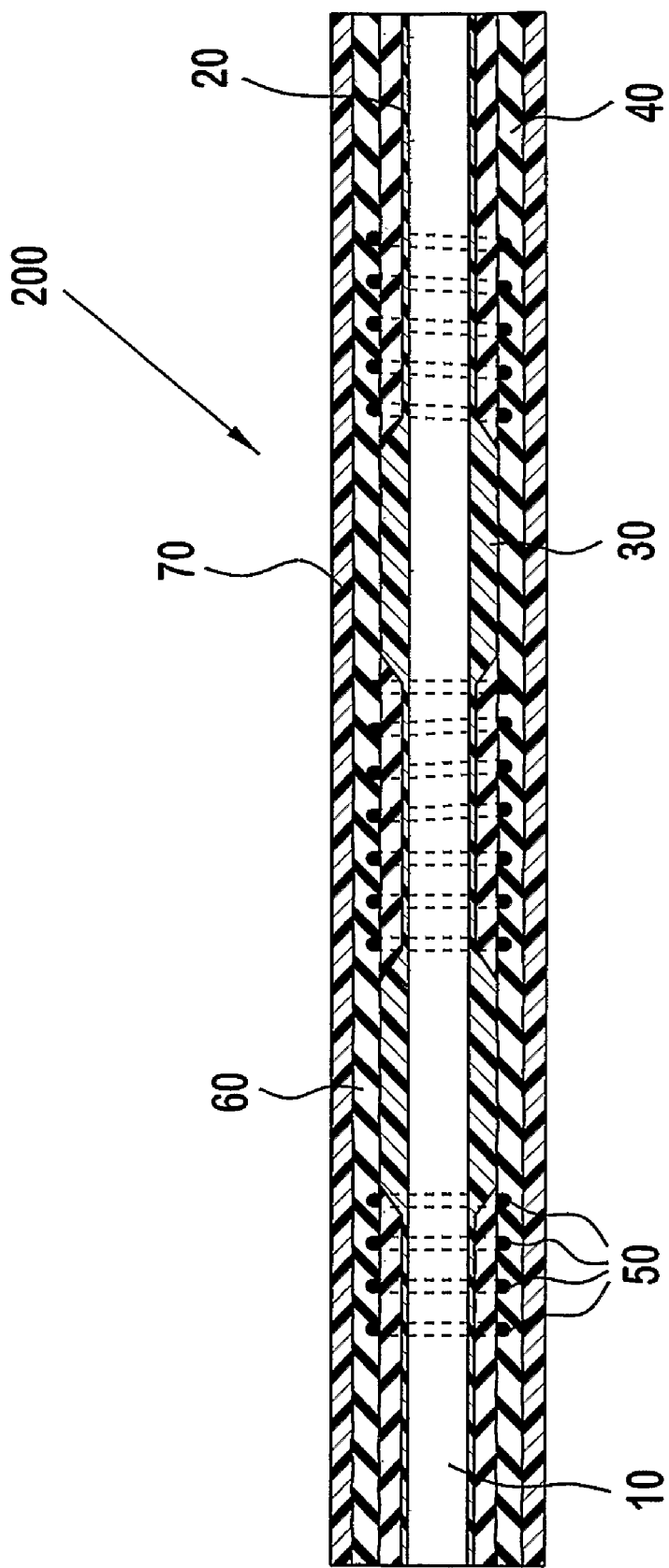
FIG. 12 is an illustration of another embodiment of an ePTFE AV graft according to the present invention.

FIGS. 11-14 illustrate examples of other preferred embodiments of an ePTFE AV graft, each of which incorporate some or all of the layers described in FIG. 10. FIG. 11 is a cross-sectional depiction of an ePTFE AV graft 100, in which an ePTFE substrate 10 is coated along its length by a base layer 20. On top of the base layer 20 at axially spaced apart locations is a sealant layer 30, a foam layer 40 being disposed over the sealant layer 30 such that the foam layer 40 comes in contact with the base layer 20 in areas substantially devoid of the sealant layer 30. Over the foam layer 40, beading is spiraled around a middle portion of the graft 100, creating a beading layer 50 and another foam layer 60 is applied. Around the foam layer 60, a wrap layer 70 is positioned by wrapping a material such as ePTFE tape (as discussed above), which can be wrapped helically. FIG. 12 is a cross-sectional depiction of an ePTFE AV graft 200, which is similar to ePTFE AV graft 100, the difference being that the beading layer 50 includes beading spiraled over spaced apart lengths of a middle portion of the graft 200 such that the beading is positioned in the locations where gaps are present in the sealant layer 30 (i.e., the beading does not overlap lengths of the graft 200 that contain sealant 30). One advantage of this embodiment is the ability to allow a surgeon to unwind the beading of the graft from one end to any desired length in order to allow for suturing of the graft end in an anastomosis, while preserving the kink-resistance of the graft right up to the anastomosis.

Figure 13:
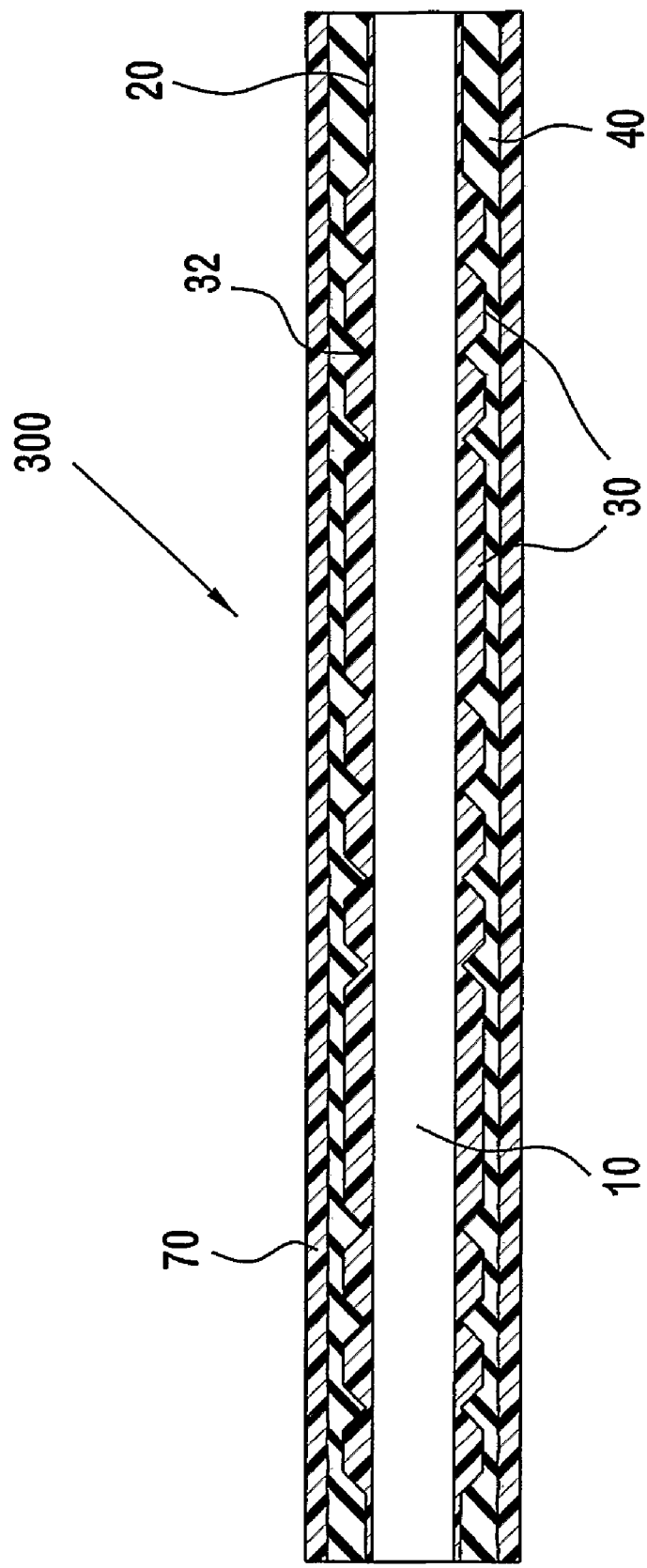
FIG. 13 is an illustration of yet another embodiment of an ePTFE AV graft according to the present invention.
Figure 14:
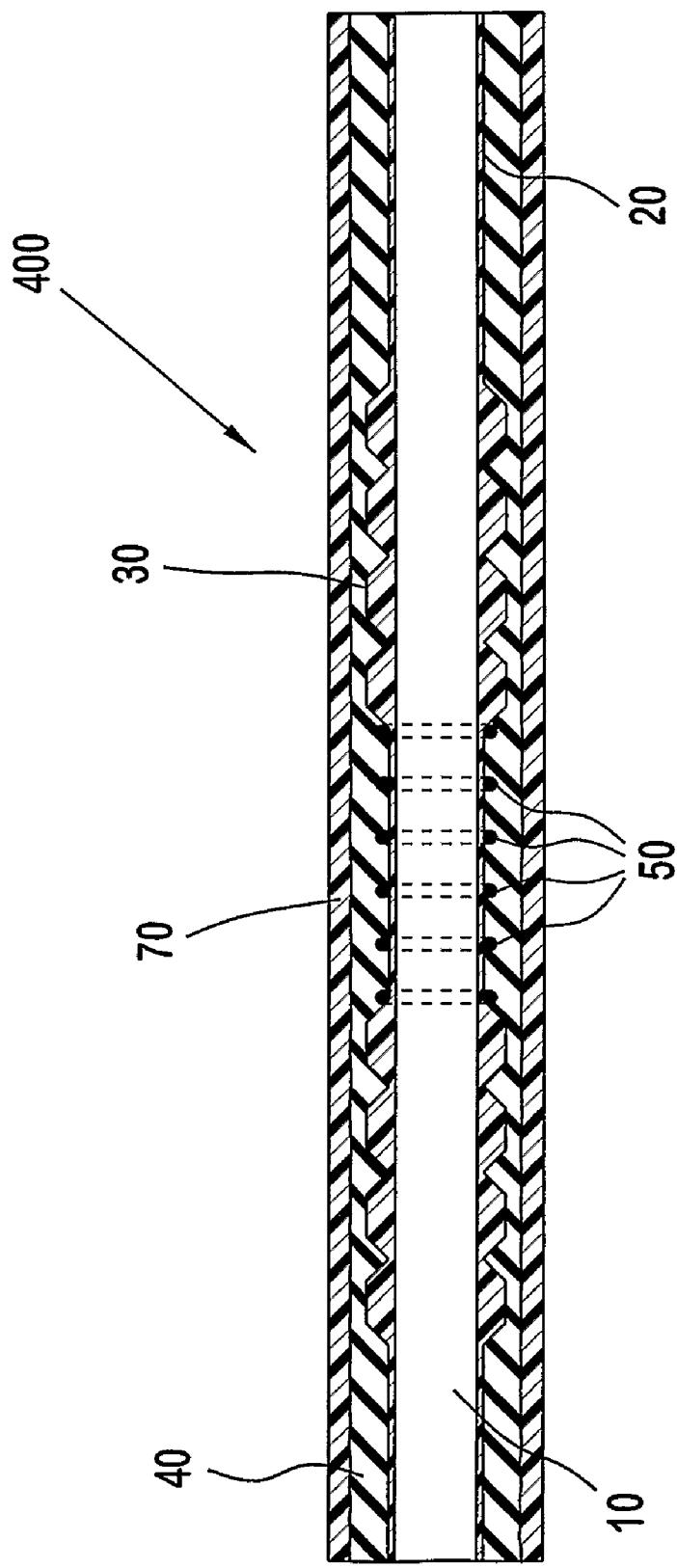
FIG. 14 is an illustration of still another embodiment of an ePTFE AV graft according to the present invention.

FIG. 13 is a cross-sectional depiction of an ePTFE AV graft 300, having a base layer 20 over an ePTFE substrate 10. In this embodiment, the sealant layer 30 positioned over the base layer 20 is continuous along a middle portion of the graft 300 with "V" shape grooved sections 32 cut down to the base layer 20. As illustrated, the grooved sections 32 are spaced apart in three small intervals followed by one long interval. Such intervals, however, could be patterned in numerous different ways to achieve desired flexibility and kink-resistance for the graft 300. A foam layer 40 is disposed over the sealant layer 30, followed by a wrap layer 70. FIG. 14 is a cross-sectional depiction of an ePTFE AV graft, having a sealant layer 30 similar to that of FIG. 13, but in place of the long interval of sealant 30 in a middle portion of the graft 300, a beading layer 50 is positioned in a middle portion of the graft 400.

It should be appreciated that each of the above-described grafts may also incorporate one or more longitudinal orientation lines (e.g., one or more blue stripes) along an outer surface thereof to ensure proper alignment (no twisting) during implantation. The orientation line or lines may also assist during manufacture to ensure that the graft is not twisted when mounted on a rotating mandrel or the like (to avoid, for example, a graft with non-homogeneous characteristics). For example, the ePTFE substrate for the self-sealing vascular grafts discussed herein may be manufactured with one or more colored (e.g., black, blue, etc.) lines so that the alignment of the line on the mandrel onto which the substrate is placed (e.g., for further processing steps in building a self-sealing vascular graft) provides visual confirmation to the manufacturer that the graft is not twisted. The orientation line or lines may be incorporated onto the substrate using a standard co-extrusion process. The preferred orientation line or lines are made from a black, blue or green biocompatible pigment or dye. The most preferred color is blue. With respect to the one or more orientation lines incorporated onto the outer surface of a self-sealing vascular graft, a printing process can be performed. The line or lines on the substrate or outer surface of the graft may be solid lines, dashed lines, or a combination thereof to indicate the center of the graft or to indicate different regions (such as cannulation regions) of the graft. It should also be noted that, instead of a line or lines, an alphanumeric identifier or a combination of line(s) and alphanumeric identifier(s) may be printed or otherwise disposed on the ePTFE surface.

In the event that the outer surface of the self-sealing vascular graft includes ePTFE, special ink compositions are necessary to ensure adherence of the line or lines on the ePTFE surface. In one embodiment, an ink composition for an orientation line for an ePTFE surface includes a suitable polymeric binder that adheres well to an ePTFE surface, a biocompatible dye or pigment, and a solvent that dissolves a polymeric binder. In addition, the ink composition may contain inorganic white solid materials such as titanium dioxide (to adjust ink shade) and a viscosity modifier. Although many pigments or dyes may be used to make the orientation line, pigments or dyes that have a long history of human implantation are most preferred. The preferred color compounds in the ink include, but are not limited to: (Phthalocyaninato(2-)) copper, D&C Blue No. 9, D&C Green No. 5, Chlorophyllin-copper complex, oil soluble, Chromium-cobalt-aluminum oxide, Ferric ammonium citrate, D&C Blue No. 5, FD&C Blue No. 2, D&C Green No. 6, Titanium dioxide, carbon, Iron oxide, and the like. (Phthalocyaninato(2-)) copper is the most preferred blue compound. The color of the ink (e.g., black, blue, etc.) may be determined by viewing under a light having a temperature of about 6500 degrees Kelvin.

Experiment E

Figure 15:
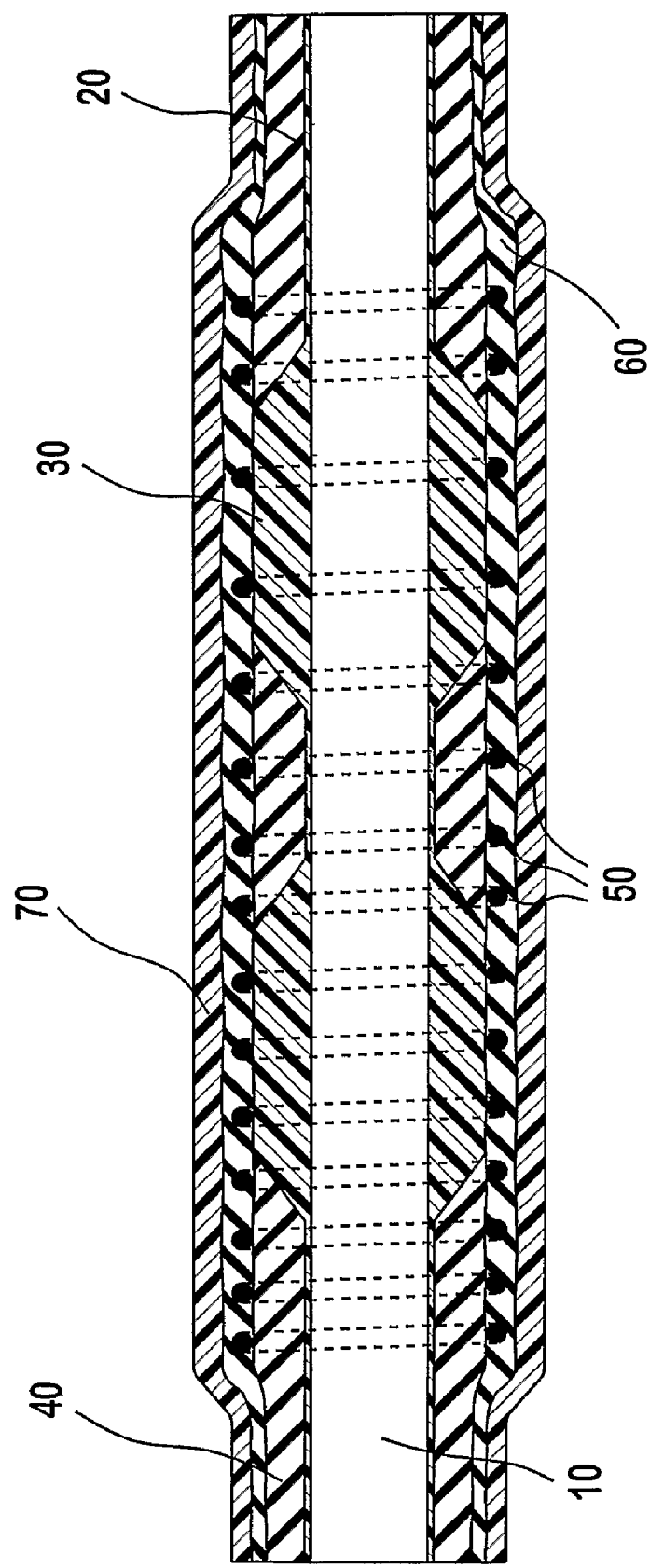
FIG. 15 is an illustration of another ePTFE AV graft according to the present invention.

Two preferred embodiments of the ePTFE AV graft were evaluated in a preliminary non-clinical in-vivo study. The grafts were evaluated in four ovine, each animal being implanted with a control graft and an experimental graft. The control grafts were polyurethane grafts having multiple layers, as described, for example, in U.S. Pat. No. 4,604,762 to Robinson, which is incorporated by reference as if fully set forth herein. Experimental grafts A-1 and A-2 were ePTFE AV Grafts as described herein, the particular configuration of at least a portion thereof depicted similar to that shown in FIG. 15 (without the outer wrap layer 70). Experimental grafts B-1 and B-2 were ePTFE AV Grafts as described herein, the particular configuration of at least a portion thereof depicted in FIG. 15 (with the outer wrap layer 70). All experimental grafts were implanted to the left femoral artery and veins. All control grafts were implanted to the contralateral side, the right femoral artery and veins.

After anesthetizing the animal, the right and left femoral arteries and veins were surgically isolated using suitable surgical techniques. Each graft was then tunneled, in a loop fashion, in the respective groin region. The animal was systemically heparinized and the grafts anastomosed in an end to side fashion using 6-0 prolene suture. At the completion of the anastomosis, the vascular clamps were removed. Following both graft procedures, a 16 GA dialysis needle was stuck through a wall of the experimental graft for five minutes. The needle was then removed and blood loss and hemostasis time were measured. The dialysis needle puncture procedure was then performed on the control graft and measurements were taken. Following recordation of desired measurements, the incisions were closed in standard fashion and the animal recovered from anesthesia.

Animals were placed on aspirin (81 mg/day) for 14 days. Grafts were evaluated for palpable thrill (as understood by one skilled in the art) at 7 days. At 13 days, the animals were anesthetized, the dialysis needle puncture tests were repeated through the skin, and angiograms were performed on both grafts. The animals were then euthanized and the grafts were perfusion fixed (in-situ) with 10% formalin and explanted for histologic evaluation. Observations regarding abluminal tissue ingrowth were conducted at explant and it was noted that the experimental grafts A-1 and A-2 that were not wrapped with an outer ePTFE layer had very little, if any, tissue ingrowth. Cannulation times (to hemostasis) and blood loss are presented on the following page in Table 6. The averages for the experimental grafts were lower that that of the control, although there was no statistical difference in pre-explant blood loss (p=0.7403) for n=6.

As can be seen in Table 6, the experimental grafts had a much shorter cannulation time in both implant and explant procedures and also achieved similar blood loss in the explant procedure when compared to the control grafts. This is significant, given the many advantages enjoyed by ePTFE over polyurethane (PU) for use in AV grafts, which are believed to include, but are not limited to: 1) ePTFE has a 25 year clinical history working well as a blood conduit compared to 3 year clinical history for PU in the US; 2) ePTFE provides better degradation resistance than PU; 3) ePTFE provides better kink resistance than PU; 4) ePTFE is easier to thrombectomize (pull clot out of graft) than PU due to its low coefficient of friction, 5) ePTFE grafts can be tunneled without a sheath, whereas PU grafts must be used with a sheath due to the high coefficient of friction of PU.

TABLE 6

| IMPLANT OVINE ID | FEM. LOCATION | GRAFT ID | CANN. TIME (sec) | CANN. BLOOD LOSS (g) | | |
|---|---|---|---|---|---|---|
| 387-B | R | Control 1 | 3:00 | 0.99 | | |
|  | L | Experimental 1-A | 3:45 | 6.91 | | |
| 141-P | R | Control 2 | 8:19 | 5.83 | | |
|  | L | Experimental 1-B | 0:50 | 2.00 | | |
| 756-B | R | Control 3 | 13:05 | 7.55 | | |
|  | L | Experimental 2-A | 3:41 | 6.92 | | |
| 125-P | R | Control A | 3:00 | 0.66 | | |
|  | L | Experimental 2-B | 3:15 | 6.97 | | |
|  |  |  | Cann Time (min:sec) | Blood Loss (g) | Blood Loss StDev | |
|  |  | Control Averages (n = 4) | 6:51 | 3.76 | 3.460 | |
|  |  | Experimental Graft Averages | 2:52 | 5.70 | 2.467 | |
| EXPLANT OVINE ID | FEM. LOCATION | GRAFT ID | 1st CANN. TIME (sec) | 1st CANN. BLOOD LOSS (g) | 1st CANN. TIME (sec) | 1st CANN. BLOOD LOSS (g) |
| 387-B | R | Control 1 | 3:00 | 0.117 | n/a | n/a | Occluded |
|  | L | Experimental 1-A | 1:09 | 0.048 | n/a | n/a | Occluded |
| 141-P | R | Control 2 | 2:25 | 0.385 | 0:51 | 0.055 |
|  | L | Experimental 1-B | 0.46 | 0.070 | 0:38 | 0.013 |
| 756-B | R | Control 3 | 1:02 | 0.022 | 1:18 | 0.029 |
|  | L | Experimental 2-A | 0:41 | 0.025 | 1:00 | 0.004 |
| 125-P | R | Control 4 | 0:58 | 0.131 | 0:43 | 0.073 |
|  | L | Experimental 2-B | 0:34 | 0.128 | 0:45 | 0.364 |
|  |  |  | Cann Time (min:sec) | Blood Loss (g) | Blood Loss StDev. | |
|  |  | Controls (except #1, n = 6) | 1:12 | 0.12 | 0.138 | |
|  |  | Experimental Grafts (except #1, n = 6) | 0:44 | 0.10 | 0.137 | |

One preferred example of an ePTFE AV graft produced according to the description provided is now described. An ePTFE substrate with a carbon lined inner surface is extruded with an orientation line (also made of carbon) and longitudinally expanded such that the final internodal distance (IND) is from about 10 microns to about 40 microns and the wall thickness is from about 200 microns to about 300 microns, preferably about 260 microns. The ePTFE substrate is positioned over a mandrel (e.g., having a diameter of about 6.3 mm) and the mandrel is rotated as two passes of a polycarbonate polyurethane are applied. The polyurethane is applied using a Binks Model 2001 spray gun with a nozzle orifice diameter less than about 1 mm, the polyurethane and a solvent, such as THF, (with non-oxidizer type inhibitor) being pressurized from the top of the spray gun and mixing with ambient air (although in one embodiment nitrogen is used in place of air) when the polyurethane is sprayed from the nozzle of the spray gun. The spray gun is spaced from the ePTFE substrate from about 2 inches to about 15 inches, preferably less than about 3 inches, while the polyurethane is sprayed onto the substrate. In the first pass, the mandrel is rotated from about 150 rpm to about 260 rpm, while in the second pass, the mandrel is rotated from about 350 rpm to about 675 rpm, preferably about 435 rpm. This forms a sealant layer or coating on the graft, having a thickness of preferably about 100 microns.

The first pass of polyurethane, which is initially dissolved in solvent as described above until a desired viscosity has been achieved (the length of the polyurethane strands varies with the viscosity—higher viscosity results in longer strands), is applied to the outer wall of the substrate (with some polyurethane penetrating into the outer wall) until a base coat of polyurethane has been applied, having a thickness of about 20 microns to about 40 microns. It should be noted that in some circumstances, the polyurethane, such as polycarbonate polyurethane, should first be heated in order for it to dissolve in the solvent. The resulting structure (substrate and first pass of polyurethane) is then longitudinally compressed (e.g., by hand) and the second pass is applied, in which additional coats of polyurethane are applied over the substrate and base coat of polyurethane in the same manner (but with faster rotation of the mandrel) until the total thickness of the polyurethane sealant layer is about 100 microns (a laser micrometer is used to verify thickness).

A polyurethane foam layer is then applied over the polyurethane sealant layer, having a thickness of about 700 microns, such that the total wall thickness of the graft structure following the application of the foam layer is from about 1 mm to about 1.1 mm. In a preferred embodiment, the foam layer has a thickness equal to the thickness of the ePTFE substrate, or in a more preferred embodiment, the foam layer has a thickness two times the thickness of the ePTFE substrate, and in a most preferred embodiment, the foam layer has a thickness greater than two times the thickness of the ePTFE substrate. The foam layer is applied by spraying polycarbonate polyurethane onto the sealant layer at a distance of about 12-20 inches and preferably at a distance of about 15 inches. Following application of the foam layer, the graft structure is placed in an oven set at an air temperature of about 50° C. to about 70° C. for about 1 hour to about 24 hours, preferably about 50° C. air temperature for about 15 hours, to cure (i.e., to re-establish the hydrogen bonds that were broken down), after which, a beading of polyurethane with barium sulfate (which provides radiopacity for visualization) is helically wrapped over the cured graft structure. The beading can have a variety of cross-sectional shapes, including round, oval, etc., but in a preferred embodiment the beading has a rectangular shape.

More specifically, in a preferred embodiment the beading is made of Carbothane® PC-35 (hardness of 72 Shore D) with 20% barium sulfate filler (to increase rigidity), supplied by Polymer Engineering Group, Tempe, Ariz., having a rectangular cross-sectional shape in which the longer side is about 1 mm and the shorter side is about 500 microns, the longer side being positioned against the outer surface of the graft. In a preferred method of applying the beading to a graft, the beading is preloaded by placing under tension of about 500 grams of force as it is wound through a solution of solvent and about an outer surface of the graft with adjacent windings of the beading being spaced from about 1 mm to about 2 mm apart. The wrapping is done under tension so that the beading becomes embedded into the foam layer. Next, another foam layer is applied, resulting in an overall wall thickness from about 1 mm to about 5 mm, and most preferably, the bead spacing over the area to be cannulated is about 4 mm and the center flex beading is about 2 mm. Over this foam layer is applied an ePTFE tape, which is preferably wrapped helically so that edges overlap somewhat. The ePTFE tape wrapping has the same IND as the substrate (i.e., about 10 microns to about 100 microns), but has a much thinner wall of about 90 microns to about 300 microns. The final thickness of the ePTFE graft is from about 1 mm to about 2 mm, preferably about 1.5 mm.

As the ePTFE tape is wrapped, solvent is simultaneously applied to assist in bonding the tape to the foam (THF or other aprotic solvent is believed to dissolve polyurethane, such that when a small amount is applied during the wrapping process, a mechanical bond is developed therebetween). Tension (e.g., about 100 gram-force to about 200 gram-force) is applied during the wrapping process, which results in the polyurethane working its way into the ePTFE microstructure to assist in the bonding. In this example, the overlapping regions of ePTFE tape do not bond to one another and instead bond to the underlying polyurethane foam, which can allow for longitudinal compliance. However, in another embodiment, the overlapping regions of the tape are adhered to one another. The wrapping of the beading and/or the tape under tension is believed to increase the sealing response of the graft. An optional orientation line can then be applied longitudinally over the length of the graft. The ends of the graft, which to this point have remained uncovered are now covered with a layer of polyurethane, followed by a helical wrap of beading, which is applied at this stage so that a clinician can remove the beading, if desired, without affecting the embedded beading layer. The beading is applied with solvent to aid in bonding.

Another preferred embodiment, in which the processing methods and equipment described above are utilized unless noted otherwise, is now described. An ePTFE substrate with a carbon lined inner surface is extruded with an orientation line (also made of carbon) and longitudinally expanded such that the final internodal distance (IND) is from about 10 microns to about 40 microns and the wall thickness is from about 100 microns to about 500 microns, preferably about 200 microns. The ePTFE substrate is positioned over a mandrel and the mandrel is rotated as two passes of a polycarbonate polyurethane with solvent are applied to the entire length of the substrate. After the first pass, the substrate is longitudinally compressed about 20% and maintained at this length while the second pass is applied to the entire substrate length, whereby the substrate remains at about 80% of its original length due to the effects of the polyurethane. The two passes of polyurethane form a sealant layer on the graft, having a thickness from about 10 microns to about 150 microns, preferably about 100 microns.

A first polyurethane foam layer is then applied over the polyurethane sealant layer as described above. This first foam layer is applied only to a mid-portion of the substrate, such that each end of the substrate is free of the first foam layer. The distance from the edge of each end of the substrate to the first foam layer is up to about 5 cm. Following the application of the first foam layer, a length of a first beading of polyurethane with barium sulfate is helically wrapped (under tension as described above) over the mid-portion of the substrate containing the first foam layer. The first beading has an elliptical cross-sectional shape with dimensions in the range of about 200 microns to 600 microns high and 200 microns to 1200 microns wide. Evaporation (e.g., by ambient temperature or by heat) is provided to remove the solvent generally before wrapping of the beading. Next, a length of a second beading is helically wrapped (under tension as described above) over each end of the first foam layer, from about 5 cm from the edge of the substrate to about 6 cm from the edge of the substrate. This second beading also has an elliptical cross-sectional shape (which can be circular if the two foci of the ellipse are identical), but has a cross-sectional area smaller than that of the first beading (e.g., a diameter of about 100 microns). After application of the second beading, a second foam layer is applied over the first foam layer and beading along the mid-portion of the substrate, the second foam layer substantially covering the first foam layer without extending longitudinally beyond the first foam layer. The total combined thickness of the first and second foam layers is from about 300 microns to about 1500 microns, preferably about 700 microns.

An ePTFE member, preferably a length of ePTFE tape, is then wrapped about the combined foam layers under tension and passing over or through a dispensing apparatus that applies solvent to the tape prior to the tape contacting the combined foam layers. The edges of the tape preferably overlap somewhat. The ePTFE tape has the same IND as the substrate (i.e., about 10 microns to about 40 microns), but has a much thinner wall of about 100 microns to about 300 microns, preferably about 260 microns. Another length of the second beading is then helically wrapped over each end of the substrate, from about the edge of the substrate to about the edge of the ePTFE tape (which is over the combined foam layers), or over a distance of about 6 cm on each end of the substrate. The two ends of the substrate (i.e., a length of about 6 cm from each edge) are then rapidly dipped in solvent. Two ePTFE generally tubular sleeves each having a length of about 6 cm are prepared and "screwed" over the ends of the substrate (i.e., rotated with force applied so that the sleeves move in a direction toward the mid-portion of the substrate, the second beading acting as "threads") until the second beading is entirely covered and the sleeve extends partially over the edges of the ePTFE tape. The sleeved ends are then rapidly dipped in solvent and the graft is placed in an oven set at about 50° C. air temperature for a time in the range of about 14 hours to about 16 hours.

Figure 16A:
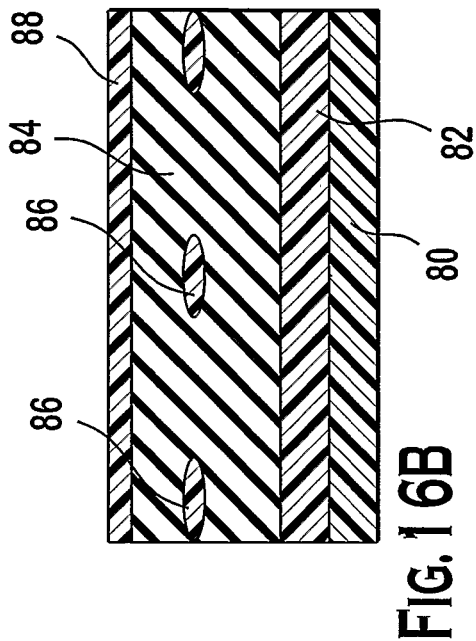
FIG. 16A is a longitudinal cross-sectional view of a mid-portion of a first preferred embodiment of an ePTFE AV graft.
Figure 16B:
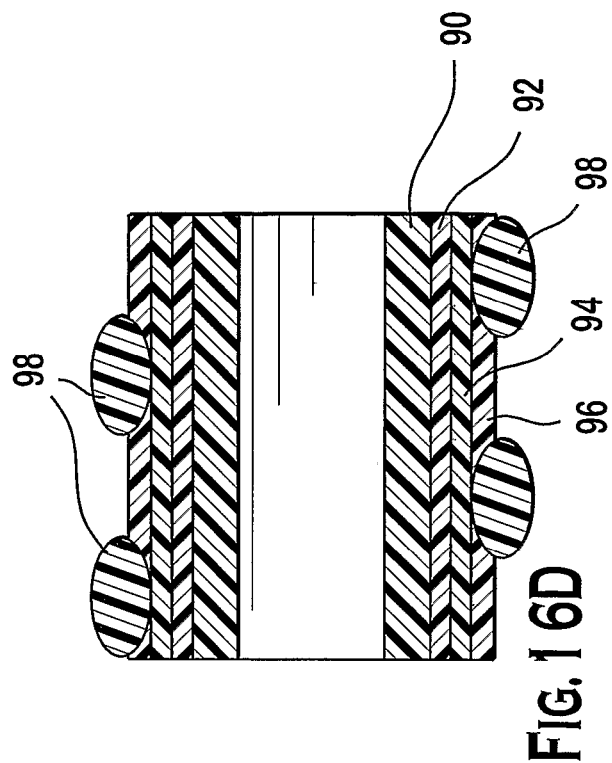
FIG. 16B is a longitudinal cross-sectional view of a mid-portion of a second preferred embodiment of an ePTFE AV graft.
Figure 16C:
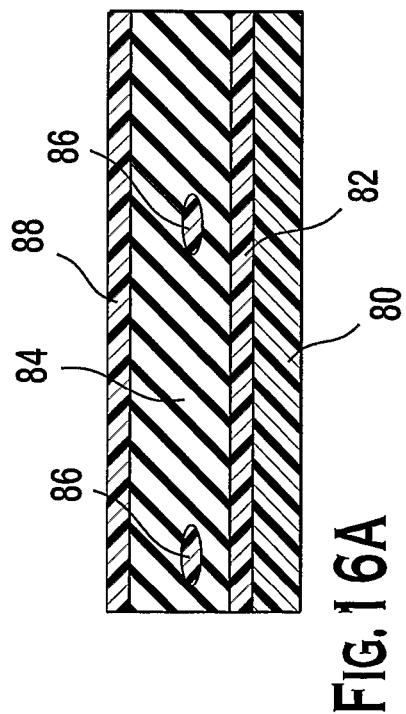
FIG. 16C is a longitudinal cross-sectional view of an end design of the first preferred embodiment of an ePTFE AV graft.
Figure 16D:
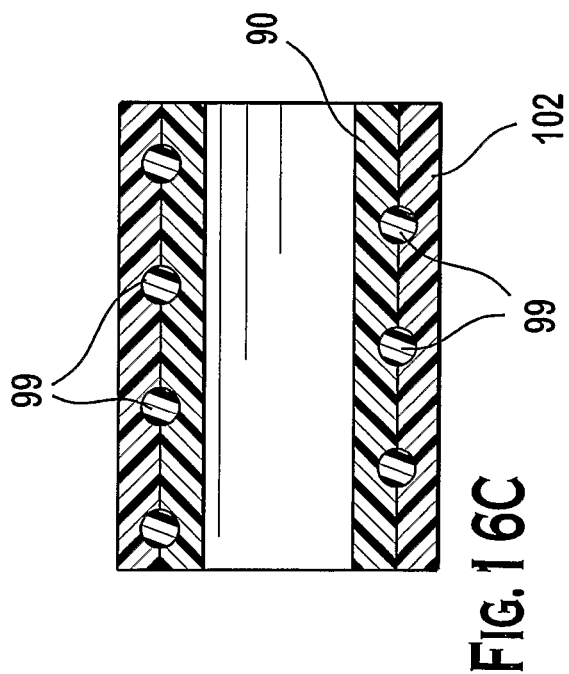
FIG. 16D is a longitudinal cross-sectional view of an end design of the second preferred embodiment of an ePTFE AV graft.

FIGS. 16A-16D illustrate embodiments of ePTFE AV grafts, with FIG. 16A and FIG. 16C representing, respectively, the currently preferred mid-portion and end design. FIGS. 16B and 16D illustrate a previous preferred mid-portion and end design of an ePTFE AV graft. Referring first to FIGS. 16A and 16B, the mid-portion includes an ePTFE substrate 80, over which is disposed a sealant layer 82 (which could include one or more layers as described herein), over which is disposed/formed a foam layer 84 (which, again, could include one or more layers as described herein). Embedded in the foam layer 84 is a beading 86 and adhered to the surface of the foam layer 84 and covering the foam layer 84 is an ePTFE member 88. The graft of FIG. 16A is different than the graft of FIG. 16B in at least the following ways: 1) the beading thickness is reduced about 16%; 2) the thickness of the sealant layer 82 is reduced by about 67%, 3) the beading 86 is moved about 44% closer to the sealant layer 82; 4) the thickness of the foam layer is reduced about 26%; and 5) the spacing between turns of the beading is increased about 18%. These changes resulted in a reduced profile graft that improved the functioning of the graft.

With respect to FIGS. 16C and 16D, the end design of the ePTFE AV graft was also changed to improve graft functionality and performance. In the previous end design shown in FIG. 16D, a first sealant layer 92 was dispensed over an ePTFE substrate 90, followed by an ePTFE tape layer 94, and a second sealant layer 96 disposed over the ePTFE tape layer 94. A beading 98 was then wrapped over the second sealant layer 96 and adhered thereto. In the new design shown in FIG. 16C, a beading 99 of smaller cross-sectional area than beading 98 is wrapped directly over the ePTFE substrate 90, adhered thereto by methods and processes described herein. An ePTFE sleeve 102, rather than an ePTFE tape wrap, is then pushed or screwed over the beading 99, resulting in a much lower profile for the end of the graft. The adherence of the ePTFE sleeve 102 to the ePTFE substrate 90 can also be accomplished by spiral wrapping the substrate 90 with beading 99, disposing the sleeve 102 over the beading 99, and spraying a suitable solvent such as THF onto the outer surface of the sleeve 102 so that the solvent penetrates through the outer sleeve 102 and onto the beading 99, which causes the polyurethane portion of the beading 99 to soften and form a bond to both the sleeve 102 and the substrate 90. It is believed that this technique allows for a substantial reduction in the delamination of sleeve 102 from the substrate 90 without having to spray the substrate with solvent or having to soak the beading 99 with solvent.

In the embodiment represented by FIG. 16A, the sealant or base layer 82 is approximately 0.04 mm thick and the foam layer 84 is formed by spraying a first foam layer of about 0.6 mm and drying this first foam layer before spraying a second foam layer so that the total foam layer 84 is about 1.2 mm. In the embodiment represented by FIG. 16C, the beading 90 has an average diameter of about 0.2 mm spaced apart over about 2 mm and disposed proximate the interface between the substrate 90 and the outer sleeve 102 where the outer sleeve 102 is approximately 500 microns.

As described above, a preferred embodiment of the self-sealing vascular graft has been utilized to demonstrate the ability of an ePTFE graft to self-seal under animal testing conditions. A description of the animal test protocols is provided below.

Ovine (sheep) animals were utilized for this study. Conditioned sheep are widely used and generally accepted as a model for vascular graft research (See "*In vivo patency of endothelial cell-lined ePTFE prostheses in an ovine model*" Artificial Organs August 1992 16(4):346-53; Tillman, P. et al, "Platelet function and coagulation parameters in sheep during experimental vascular surgery" Lab. Anim Sci 1981 31:263-7; Kohler, T. et al "Dialysis access failure: A sheep model of rapid stenosis" JVascSurg 1999 30:744-51). Good size match can be achieved for 6 mm diameter grafts and graft lengths up to 35 cm can easily be implanted in the carotid artery to jugular vein model. Grafts placed in the neck can be easily accessed by palpation for a thrill and examined with a hand-held Doppler. According to the study described, six experimental/test grafts (Sedona) and two control grafts (Vectra® AV Access competitive graft) were implanted in four animals. Two animals received one control (Vectra® AV Access competitive graft) and one test graft (Sedona) bilaterally, using right carotid to left jugular and left carotid to right jugular. Two animals received two test grafts (Sedona) bilaterally, using right carotid to left jugular and left carotid to right jugular.

Six experimental/test grafts made in a manner described in relation to FIGS. 16A and 16C were utilized while two commercially available grafts were utilized (sold under the trade name "Vectra®" AV in expired condition and in a sterile package with an inner diameter of 6 mm and a length of 40 cm (product code #T6040-001)). Access grafts were placed in four animals (one experimental and one Vectra® AV Access graft in each of two animals, and two experimental grafts in the remaining two animals). All grafts were of the same inner diameter and approximate length. The grafts (experimental and Vectra® grafts) were accessed (cannulated with 14 gauge needles) immediately after implant and then in a different location during one additional cannulation session taking place preferably within the first 24 hours post-implant, but at most within 48 hours post-implant. All grafts were explanted at 8 weeks post-implant, with an option to explant at 4 weeks post-implant.

The materials utilized included six sterile experimental grafts, two sterile Vectra® AV Access Grafts, four sheep 75-95 kg in body weight, two 120° AV Access Sheath Tunnelers with two sheaths, suitable surgical instruments, 6-0 prolene suture, 2-0 vicryl suture, 14 gauge dialysis needles, and 4×4 gauze pads. The Vectra® Access grafts were placed per the accompanying Information For Use (IFU) for such grafts and the experimental grafts were placed per standard procedures by a surgeon trained in vascular procedures. The placement and accessing of the grafts took place under normal conditions using standard procedures and techniques known to those skilled in the vascular art.

The following protocols were followed during the study. The animals were fasted at least 12 hours prior to surgery. A general physical examination was performed, and rectal temperature and body weight recorded prior to animal prepping and any unusual findings were reported to the Study Coordinator or Principal Investigator. The animals were pre-medicated with ketamine (10 mg/kg IV) plus valium (0.5 mg/kg IV) or Telazol (6-8 mg/kg IM). Atropine (0.04-0.4 mg/kg either IM, SQ or IV) or similar drug were given to decrease respiratory secretions and prevent bradycardia. An intravenous catheter was placed. The animal was "masked down" with isofluorane to facilitate intubation. An endotracheal tube was placed and the cuff inflated. The surgical area was clipped and surgically prepped with sterile solution such as betadine. The animal was transported to the surgical suite and placed in the dorsal recumbent position on the operating table and all legs were secured. The surgical site was prepped and draped in sterile fashion. General anesthesia was maintained with isofluorane. An intravenous drip of isotonic fluids was initiated and Cefazolin (1 gm, IV), Baytril (7.5 mg/kg) or Gentocin (2 mg/kg) IM or IV was administered prior to initiating the surgical procedure. Blood was taken for a baseline ACT (activated clotting time) and additional blood (about 5 ml to about 15 ml) may have been taken at this time and varying time points during the in life period for additional diagnostic procedures. No sedation was necessary for diagnostic post implant blood draws.

The following implant procedures were followed in the study. A loop type arteriovenous shunt, between 30 cm and 40 cm in length, was created using the test or control graft. The graft was tunneled subcutaneously in a loop fashion using the 120 degree sheath tunneler provided. The right and left carotid arteries and jugular veins were surgically isolated and controlled. The two AV grafts were tunneled in loop fashion in the appropriate area of the neck of the animal. Prior to tunneling, each graft was prepared as per IFU/general implantation guidelines. Sedona/experimental grafts were placed per standard procedures by a surgeon trained in vascular procedures. The animal was administered heparin (about 100 u/kg, IV) as needed to maintain an ACT above 250. Subsequent heparin boluses were given in varying doses to maintain the target ACT. The first carotid artery and jugular vein (right carotid and left jugular or left carotid and right jugular) were isolated and controlled, and the graft anastamosed in standard fashion using 6-0 prolene suture. The time was recorded from the start of the first suture placement until completion of both anastamoses. The graft was purged of air by venous back bleeding, the area dried of excess blood and fluid, and clamps/loops were removed. Graft handling was evaluated and recorded on separate data sheets. Once the first AV graft procedure was completed and the graft demonstrated hemostasis, prior steps described above were repeated for the contralateral graft implant. All incisions were closed with 2-0 vicryl suture and the area was infiltrated with local analgesic. The ovine were recovered and returned to normal housing as per standard procedures. Animals were monitored daily and given aspirin (325 mg, PO) daily.

Hemostasis of graft puncture was evaluated after completion of each implant, but before the animal recovered from anesthesia, and at one additional session preferably within 24 hours post implant, and at maximum within 48 hours post implant. The experimental study graft (Sedona) and the Vectra® control graft were cannulated in the same manner. Needle punctures at both implant and needle punctures at the additional session (preferably within 24 hours post implant) were all through the skin. Evaluation for hemostasis or bleeding of the cannulated site was performed in this test at implant by puncturing the graft through the skin in the cannulation regions prior to recovering the animal from anesthesia. At implant, this cannulation session consisted of two needles left in for 5 seconds (one on the arterial cannulation side and one on the venous cannulation side) and two needles left in for 1 hr (one on the arterial cannulation side and one on the venous cannulation side). Results were recorded for each session. The second needle puncture session (performed preferably within 24 hours of implant, and at a maximum within 48 hours after implant) accessed the grafts through the skin. This cannulation session consisted of two needles left in for 1 hour (one on the arterial cannulation side and one on the venous cannulation side) and two needles left in for 3 hours (one on the arterial cannulation side and one on the venous cannulation side). Results were recorded for each session.

The activated clotting time (ACT) was measured and maintained above 250, and the most recent ACT that was taken prior to pulling each of the 5 sec, 1 hour, or 3 hour needles was recorded appropriately, along with the time the ACT was drawn. The time each needle was pulled was recorded, and can thus be compared to the time of the latest ACT. Twenty pre-weighed 4×4 gauze pads were prepared for each needle access and the weights appropriately recorded. For evaluations after the surgery, the graft was also palpated and any tissue abnormalities, including swelling, infection and seroma, were noted. Photographs may have been used to record appearance of the tissue and/or grafts in selected animals. For needle puncture tests performed during the post-implant session, the animal was anesthetized per standard procedures and then the grafts were accessed with standard dialysis access needle sets (14 gauge) through the skin. Previous sites for needle puncture were avoided. For all needle puncture tests, a heparin-lock was utilized, and prior to pulling the needle, a confirmation of graft patency was made by drawing back on the syringe to observe that blood was drawn into the tubing. The needles were left in place for the appropriate time duration. The centermost 6 cm (Centerflex Region) of the graft was avoided for puncturing.

Needles were directed toward the anastomosis (i.e., on the arterial side, needles were directed against the flow, and on the venous side, needles were directed with the flow). Each needle was removed while simultaneously applying pressure with a 4×4 pad that had been previously weighed. Pressure was applied using standard procedures to needle puncture site using 4×4 pads, and the gauze checked for hemostasis (no visible blood from the needle puncture site) at 2 minutes after needle removal. If hemostasis was not achieved, pressure was reapplied with the gauze for another 2 minutes and checked for hemostasis at 4 minutes after needle removal. If hemostasis was still not achieved, pressure was reapplied with the gauze for another 1 minute and checked for hemostasis at 5 minutes after needle removal, and every minute thereafter, re-applying pressure after each check until hemostasis was reached. Pre-weighed 4×4 pads were replaced as are they were used. The time for hemostasis was noted and recorded (no visible blood from puncture site). All twenty 4×4 gauze pads were weighed and the original weight was subtracted to determine blood loss in grams. The above steps were repeated using a new puncture site until completion of all cannulations, at the appropriate needle dwell time durations, for the session at implant, and for the session at preferably 24 hours but at maximum 48 hours post-implant. The administered heparin was re-administered as needed to maintain an ACT above 250.

The above steps were repeated until all cannulations described above were completed for both grafts. It is noted here that for studies, such as the study disclosed above, needle placements can and should be made staggered in time in order to minimize the overall time for the needle puncture sessions. Any differences between the grafts such as needle force penetration, ability to feel pulse and/or "thrill," and ability to cannulate easily should be noted. All incisions (for the needle puncture sessions conducted at implant) were closed and the area infiltrated with local analgesic. The ovine were returned to normal housing as per standard procedures. Animals were monitored daily.

At eight weeks, the following protocols were followed. The ovine were pre-anesthetized and prepared for surgery as described above. The ACT was measured, the graft palpated and any tissue abnormalities including swelling, infection and seroma were noted. Photographs were used to record appearance of the tissue and/or grafts. Animals were heparinized with 10,000 units of heparin and completion angiograms were obtained as a final assessment of graft patency for both the experimental study graft and the Vectra® control. Tables 7 and 8 show the collected data for the study.

TABLE 7

Experimental Grafts

| Needle Dwell Time | Hemostasis at 2 minutes | Hemostasis at 4 minutes | Hemostasis at greater than 4 minutes |
|---|---|---|---|
| 5 seconds | 10 discrete punctures | | |
| 1 hour | 15 discrete punctures | 2 discrete punctures | 1 discrete puncture (5 minutes) 1 discrete puncture (6 minutes) 1 discrete puncture (7 minutes) |
| 3 hours | 9 discrete punctures | 1 discrete puncture | |

TABLE 8

Vectra ® Graft

| Needle Dwell Time | Hemostasis at 2 minutes |
|---|---|
| 5 seconds | 2 discrete punctures |
| 1 hour | 8 discrete punctures |
| 3 hours | 4 discrete punctures |

The data in Tables 7 and 8 is believed to demonstrate that a self-sealing ePTFE composite graft can be obtained heretofore that performs virtually as well as a self-sealing non-ePTFE graft such as the Vectra® polyurethane graft. In other words, the data show that, with a five seconds needle dwell, hemostasis is achieved in generally the same time frame as the known self-sealing polyurethane graft; with a one hour needle dwell, hemostasis is also generally achieved within two minutes for the majority of needle punctures; and, with a 3 hour needle dwell, the majority of needle punctures achieved hemostasis within two minutes. Thus, a self-sealing ePTFE graft can be obtained that includes an ePTFE surface, which defines an interior volume that extends from a first opening to a second opening. The surface defines a perimeter of the first opening and perimeter of the second opening coupled to at least one of an artery and vein of an animal to permit blood flow through the first and second openings. The self-sealing graft includes means for achieving hemostasis of blood flow from a vein or artery of a sheep other than through the first and second openings within about two minutes subsequent to withdrawal of a 14 gauge needle punctured through the surface and disposed in the interior volume over a predetermined duration of about five seconds, one hour, and three hours. The means for achieving hemostasis can include at least a polyurethane foam. The means for achieving hemostasis can also include multiple polyurethane layers. Most preferably, the means for achieving hemostasis can include multiple polyurethane layers with a structural support member disposed in circular path about the ePTFE surface.

Self-Sealing Cuff Graft

The various graft configurations described herein can also have one or more cuffs provided to aid in attachment to a blood vessel. Vascular grafts with cuffs, cuff configurations and methods and apparatuses for making such cuffs and cuff grafts for attachment to blood vessels are described in U.S. Pat. No. 6,273,912 to Scholz et al., U.S. Pat. No. 6,746,480 to Scholz et al., U.S. Application Publication No. US 2004/0210302 to Scholz et al., U.S. Pat. No. 6,190,590 to Randall et al., U.S. Pat. No. 6,203,735 to Edwin et al., U.S. Pat. No. 5,861,026 to Harris et al., U.S. Pat. No. 6,221,101 to Harris et al., U.S. Pat. No. 6,589,278 to Harris et al., and U.S. Application Publication No. US 2004/0064181 to Harris et al., each of which is commonly assigned and incorporated by reference as if fully set forth herein.

Figure 17:
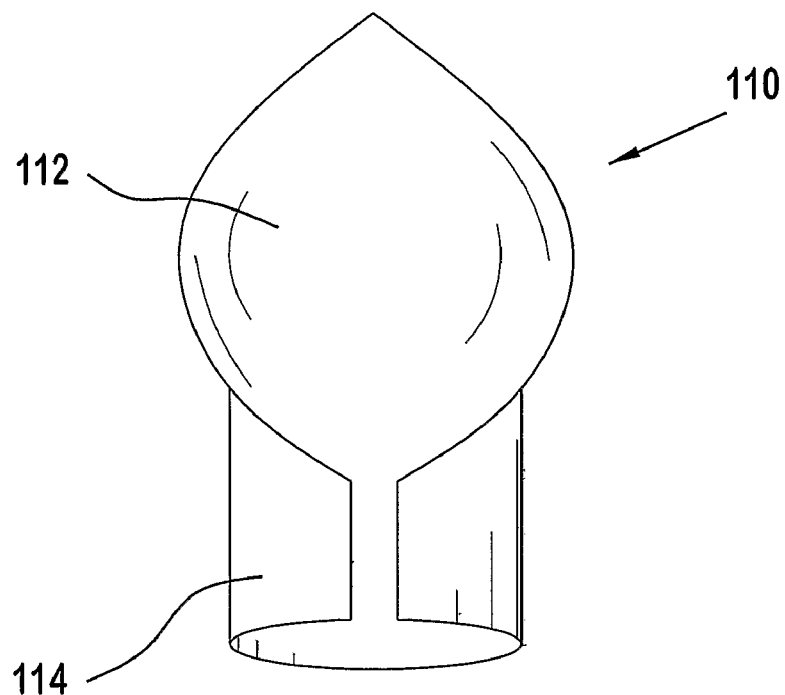
FIG. 17 is a back perspective view of an attachable cuff.

The cuff can be made of ePTFE or other material, such as silicone or polyurethane, and can be bonded to an ePTFE AV graft or a graft having a silicone, polyurethane or other material substrate. One example of a cuff for attachment to a graft is shown in FIG. 17, where a back view of cuff 110 illustrates a cuff section 112 and a neck section 114, wherein the neck section 114 is separated along at least a portion of its length, thus facilitating placement of the cuff over an end of a graft. The cuff 110 can then be bonded to the graft, according to the material properties of each. For instance, in the case that the cuff and graft surface for attachment of the cuff are ePTFE, the cuff can be attached via heating as is known to one of ordinary skill in the art. With respect to embodiments of the ePTFE AV graft described above, the cuff could be placed over one or both ends of the graft at various stages of manufacture. In one embodiment, as with the application of the ePTFE tape wrap, an ePTFE cuff is placed over an end of the graft that has a polyurethane layer applied thereto (e.g., base layer, foam, etc.). A suitable solvent, such as for example, an aprotic solvent including dimethylacetamide (DMSE), dimethylforamide, THF, or their mixtures, is then applied to the neck section of the cuff to dissolve the polyurethane underlying the neck section, which results in bonding of the cuff to the graft. Beading or other processing steps, as discussed herein, would then be possible over the cuff/graft junction.

In another embodiment, a cuff graft is separately formed from an ePTFE AV graft as described herein. The tubular portion of the cuff graft is then attached to the ePTFE AV graft by stretching the wall of the open end of the tubular portion (e.g., via use of an expansion tool) and sliding over one of the ends of the ePTFE AV Graft. In one embodiment, the ePTFE AV graft has external beading, and the open end of the tubular portion of the cuff graft is slid over the ePTFE AV graft until the tubular portion reaches the external beading portion of the ePTFE AV Graft, at which point the tubular portion of the cuff graft is rotated or "screwed" over the external beading. The inner surface of the tubular portion of the cuff graft can have an adhesive thereon to aid in bonding or further bonding can be carried out after the initial attachment step, if desired.

In another embodiment, a self-sealing cuff graft can be created by impregnating polyurethane or a like polymer into the microstructure of an ePTFE cuff graft by vacuum deposition, spray coating, or dip coating procedures as known to a person skilled in the art. Once the polyurethane or like polymer has been introduced, any excess polymer is removed from the exterior of the graft to allow the polyurethane to be formed in the interstices between the nodes and fibrils of the ePTFE. Another embodiment involves spray coating an ePTFE cuff graft with a combination of polymer and solvent as discussed herein, followed by applying an ePTFE tape or patch thereover to create an ePTFE/polymer/ePTFE laminate. In another embodiment, a self-sealing cuff graft is created by connecting a cuff having a neck portion to a graft, dip-coating the graft in a sealant material (e.g., polyurethane) up to the connection point between the graft and neck portion of the cuff, dip-coating both the graft and neck portion in a sealant material (up to the cuff), helically wrapping a beading around the sealant material over the length of the graft and neck portion, and dip-coating the beaded graft and neck portion in a sealant material (up to the cuff).

Figure 18:
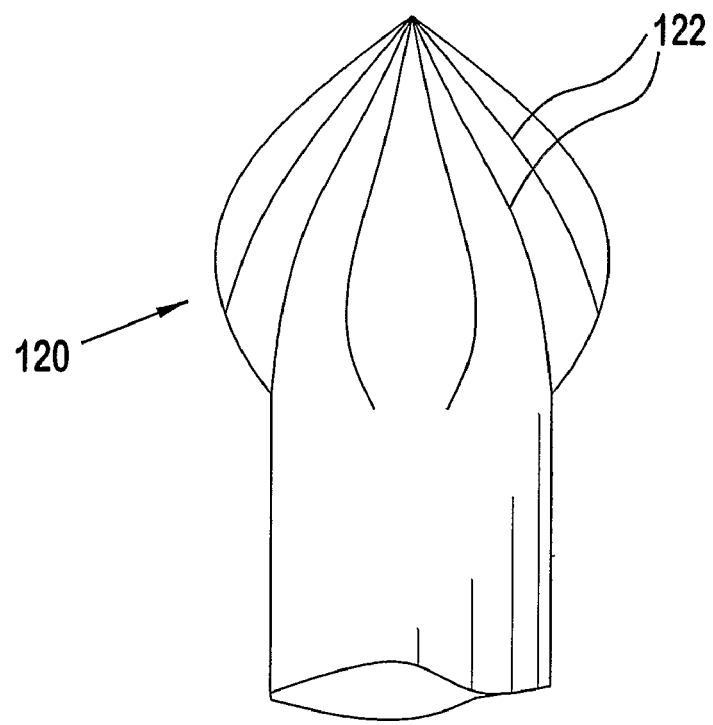
FIG. 18 is a front perspective view of a cuff portion of an ePTFE AV graft with cuff.

In yet another embodiment, the tubular body portion of an ePTFE cuff graft is utilized as the ePTFE substrate for the various processing steps described herein to impart self-sealing, kink-resistance, etc. to the graft. The cuff portion of the ePTFE cuff graft can be on one or both ends of the graft and can have a sealant layer applied thereto or can remain unprocessed. For example, the cuff portion can have a polyurethane coating to maintain the cuff shape. In the event that the cuff portion has a sealant layer applied thereto, the sealant material (e.g., polymer) can be applied in a pattern. In one embodiment, a polymer applied to the cuff portion of an ePTFE AV graft (with cuff) is done so in a pattern of "ridges" on the top of the cuff, as illustrated in FIG. 18. The polymer, such as, for example, polyurethane, at the ridge portions 122 of the cuff 120 provide suture regions for a clinician to mitigate or prevent suture hole bleeding upon attachment to a blood vessel. These ridge portions can be created, for example, by placing a mask over the cuff before the polymer is applied or by laser cutting ridges into the polymer once it has been applied to the cuff. The ridge portions can take on various configurations and be set at a variety of angles, as a person skilled in the art would appreciate. Moreover, in one embodiment the material used to create the ridges has a radiopaque substance incorporated therein so that the edges of the ePTFE cuff can be readily identified during surgery.

Although the preferred embodiments have been described in relation to Carbothane® PC-2585, available from Polymer Technology Group, other suitable polyurethanes, such as, for example, Bionate®, Chronoflex® C (Cardiotech) with a hardness of 93 Shore A, polycarbonate diol (1,6-hexanediol), 14,4-methylene bisphenyl diisocyanate urethane with 1,4-butanediol/dimethylsilane (molecular weight of the soft segment of the polyurethane of about 1000 to about 3000). The weight-average molecular weight (MW) for a suitable polyurethane (i.e., the entire polymer) is in the range of about 25,000 g/mole to about 500,000 g/mole, preferably in the range of about 40,000 g/mole to about 150,000 g/mole. In one preferred embodiment, the weight-average molecular weight is about 50,000 g/mole. Moreover, the spraying of polyurethane using a spray gun as described herein can be utilized for applications other than applying polyurethane onto a graft substrate, such as spraying a material such as polyurethane onto a stent to produce a covered stent, spraying a material such as polyurethane onto both surfaces of a stent to produce an encapsulated stent, spraying a material such as polyurethane onto a frame to create a filter, etc. In one embodiment, a thrombotic material is incorporated into the foam layer. In another embodiment, the methods, processes and materials described herein to create a graft are applied to a patch for carotid applications in order to reduce suture hole bleeding. Finally, it is noted that the beading on the graft as described herein (e.g., its stiffness properties) is believed to cause a dialysis needle or introducer sheath to deflect away from the beading and into the graft upon contact with the beading.

This invention has been described and specific examples of the invention have been portrayed. While the invention has been described in terms of particular variations and illustrative figures, those of ordinary skill in the art will recognize that the invention is not limited to the variations or figures described. For example, the ePTFE tape does not have to be utilized with the foam layer in order to achieve the self-sealing functionality of the vascular graft. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A self-sealing vascular graft, comprising:
   a tubular ePTFE substrate having a first surface and a second surface spaced from the first surface;
   a layer of sealant disposed over one of the first and second surfaces, the sealant comprising a polymeric material resistant to plastic deformation upon insertion of a puncture member through the sealant layer;
   a first layer of foam disposed over the sealant layer;
   a PTFE beading helically wrapped over the first foam layer circumscribing a longitudinal axis of the ePTFE substrate;
   a second layer of foam disposed over the PTFE beading; and
   an outer layer disposed over the second foam layer.

2. The self-sealing vascular graft according to claim 1, wherein the sealant comprises a material selected from the group consisting essentially of aromatic polycarbonate polyurethanes, polyetherurethanes, polyether/polyamide block copolymers, polydimethylsiloxane elastomers, or other silicone elastomers and combinations thereof.

3. The self-sealing vascular graft according to claim 1, wherein the sealant comprises a heat-treated aromatic polycarbonate polyurethane.

4. The self-sealing vascular graft according to claim 1, wherein the polymeric material comprises polyurethane having a weight-average molecular weight (MW) of about 50,000 g/mole.

5. The self-sealing vascular graft according to claim 1, wherein the sealant comprises particles of a material selected from the group consisting essentially of polyester, collagen, thrombin, or fibrinogen and combinations thereof.

6. The self-sealing vascular graft according to claim 1, wherein the ePTFE substrate is selected from the group consisting of a high porosity graft, a thin-wall graft and combinations thereof.

7. The self-sealing vascular graft according to claim 1, further comprising a bioactive agent incorporated into at least one of the substrate, sealant layer, first foam layer, second foam layer, and outer layer.

8. The self-sealing vascular graft according to claim 7, wherein the bioactive agent is selected from the group consisting essentially of carbon particles, silver particles, graphite particles, antibiotics, macrolide antibiotics, steroidal agents, anti-inflammation agents, antineoplastic agents, antifungals, antivirals, antibodies, genetic sequence agents, growth factors inhibitors, angiogenesis, anti-angiogenesis, proteinase inhibitors, antiproliferative compounds, or cell cycle modulators and combinations thereof.

9. The self-sealing vascular graft according to claim 1, wherein a tubular end of the graft is coupled to a flared end of a prosthetic cuff graft.

10. The self-sealing vascular graft according to claim 9, wherein the tubular end is threaded to a tubular portion of the prosthetic cuff graft.

11. The self-sealing vascular graft according to claim 9, wherein the tubular end is bonded to the tubular portion of the prosthetic cuff graft.

* * * * *